(12) United States Patent
Cornuejols

(10) Patent No.: US 6,547,728 B1
(45) Date of Patent: Apr. 15, 2003

(54) DEVICE FOR MEASURING ORGANISM CONDITION

(76) Inventor: Georges Marc Cornuejols, 1148 Westmoreland Rd., Alexandria, VA (US) 22308

( * ) Notice: Subject to any disclaimer, the term of this patent is extended or adjusted under 35 U.S.C. 154(b) by 0 days.

(21) Appl. No.: 09/646,105

(22) PCT Filed: Mar. 31, 1999

(86) PCT No.: PCT/FR99/00747
§ 371 (c)(1),
(2), (4) Date: Jan. 16, 2001

(87) PCT Pub. No.: WO99/49784
PCT Pub. Date: Oct. 7, 1999

(30) Foreign Application Priority Data

Mar. 31, 1998 (FR) .............................................. 98 03998
Nov. 24, 1998 (FR) .............................................. 98 14801

(51) Int. Cl.$^7$ ................................................ A61B 5/00
(52) U.S. Cl. ........................ 600/300; 600/481; 600/483; 600/529; 600/532; 600/538; 600/544; 600/545; 600/546
(58) Field of Search ............................... 600/300–301, 600/544–546, 481–483, 529, 532, 538

(56) References Cited

U.S. PATENT DOCUMENTS

| | | | | |
|---|---|---|---|---|
| 4,836,219 A | * | 6/1989 | Hobson et al. | 600/595 |
| 5,197,941 A | * | 3/1993 | Whitaker | 600/27 |
| 5,280,791 A | * | 1/1994 | Lavie | 600/529 |
| 5,356,368 A | * | 10/1994 | Monroe | 600/28 |
| 5,507,716 A | * | 4/1996 | LaBerge | 600/27 |
| 5,899,203 A | * | 5/1999 | Defares et al. | 600/529 |
| 5,902,250 A | * | 5/1999 | Verrier et al. | 600/515 |
| 5,928,133 A | * | 7/1999 | Halyak | 600/26 |

* cited by examiner

*Primary Examiner*—Robert L. Nasser
*Assistant Examiner*—Patricia C. Mallari
(74) *Attorney, Agent, or Firm*—Young & Thompson

(57) ABSTRACT

The device includes:

an information intake system that obtains a value representing a non-sensory biological activity of a user's body, such as the pulse or the activity of a limb, a filter for filtration of the value obtained by the said information intake device, which provides a relative position of the said value in a cycle representing a temporal variation of the said biological activity, and an output system to allow the user to know information representing the relative position, for example an alarm, a screen, or a watch hand on a dial.

19 Claims, 13 Drawing Sheets

DEVICE FOR MEASURING ORGANISM CONDITION

A device that allows a user to know information relating to one or more of his or her biological clocks.

FIELD OF THE INVENTION

The present invention relates to a device and a method that allows a user to know information relating to one or more of his or her biological clocks. A biological clock is a quasi-periodic cycle of variations of a value that represents the natural state of the user.

BACKGROUND OF THE INVENTION

The technical problem underlying the present invention is new: for multiple reasons, every individual wants to better understand his or her own biological resources and how he or she functions. The reduction in time spent at work and the development of part time work and leisure activities incites each to manage his or her activities as a function of his or her own rhythms. The technical problem underlying the present invention includes determining the values of at least one biological clock and allowing them to be known by the user.

The invention is particularly used to help the user to:
manage one or more of his or her sleep cycles, especially by using a device designed to awaken the sleeping user (devices commonly called alarm clocks);
manage pauses between periods of intense activity;
select an appropriate time to begin an activity; and
select an appropriate time to end an activity;
evaluate his or her ability, at a given moment, to effectively perform an activity;
evaluate his or her ability to effectively perform an activity of a longer duration than a biological cycle.

The inventor has asked himself about the possibility of putting a device or method that provides information regarding a user's biological clocks to the use of any individual from the general public.

The term "general public" is not to be considered herein as a simple commercial constraint without technical consequences on the problem underlying the present invention: so that the device and method envisioned by the present invention are for the "general public," their implementation must not require any medical protocol, nor restrictions imposed by individual insurance policies, nor cause the user to have to obtain help from another person, nor cause the user to follow more than a few minutes of instructions, nor impede the activity, concentration ability, or rest of the user, nor handicap the user in any way, and it must not give the user an abnormal facial appearance.

Therefore, the implementation of the present invention must not be more dangerous, less comfortable, or less discreet than other everyday objects that exist in the everyday routine of a member of the general public, such as a watch, jewelry, an alarm clock, a pillow, an electric blanket, a calculator, an electronic pocket organizer, a pocket television, a computer and monitor, a walkman, earphones, or glasses.

The terms "comfortable" and "discreet" as used herein must be used technically, as they are used in ergonomics. Some objective criteria can also be associated with each of these terms; for example, ten percent of the population that are accustomed to a physical interaction between themselves and a device similar to a particular implementation of the device envisioned by the present invention should not have their attention monopolized by the device, aside from periods of manipulation or usage of this device, throughout a day of interaction with the device. Alternatively, the same proportion of the population should, under the same conditions, have normal activity and rest.

The present invention also envisions a user friendly (human like) device and method; that is, where the time it takes the user to learn how to use the device and become accustomed to it is of the order of only a few minutes, and, in all cases, less than one hour, after which the user can return his attention to his normal routines. It should be observed that the term "human like" is a technical term in ergonomics that allows one skilled in the art to take practical measures to exclude different embodiments that are, at first glance, preferable because they are used for analyzing biological clocks, thus excluding, for example:
methods that require the placement of electrodes on the eyes, the use of rectal probes, the drawing of blood, or the analysis of excretions (see: below for the explanation of the prejudices of one skilled in the art); and
methods that impose limits on the user's freedom of movement.

In some aspects, the present invention also envisions safeguarding against accidents caused at least in part by the sleepiness of night workers or night conductors by helping the user to be more aware of his or her biological state.

Some further technical problems that aim to resolve at least some aspects of the present invention have to do with the difficulty of obtaining and processing variations in the biological or physiological state, which are relatively common in the human being, in such a manner that the result of the processing is not made void by the environment in which the device and the method of the invention is implemented, and by the eventual voluntary activity of the user.

The variation of the obtained signal can thus, at the same time, be weak in comparison to the absolute value of the signal and in comparison to the changes due to the environment and the eventual voluntary activity of the user. This expresses a technical problem common to many aspects of the present invention.

The inventor has therefore removed himself from the medical protocols linked to the analysis of biological clocks, as they are described in the book "Biological Clocks," edited in 1998 by Yvan Touitou, Excerpta media, editions Elsevier, Amsterdam, Holland. These protocols enforce the placing of electrodes, by a physician in a medical experimental laboratory, on the face or skull of the animal being examined, with limitations to its movements, its feedings, its activities, its sleeping time, and the drawing of blood or the taking of its rectal temperature. The examined animal can therefore have neither normal activity, nor normal concentration ability, nor normal rest.

The actual analysis of human biological clocks is limited to the circadian cycles or to cycles of a duration longer than a day. It is occupied mainly with ways to offset these cycles by illumination at various times and for various durations, or by injecting chemical substances in the body. The interest of many of these researches is to reduce the effects of shifted schedules for travelers suffering from jet lag.

No attempt to provide the analyzed subject with information representing an instantaneous phase (or relative position) in the cycle of variations corresponding to a biological clock has been effectuated.

On the other hand, the watches, clocks, and alarm clocks used these days provide nothing but the time and/or an alarm, and not one bit of information concerning the capacity of the user to utilize the following moments for one activity or another.

The alarm clocks used these days permit a wake up time to be chosen, but function independently of the biological functioning of the user, the time the user fell asleep, the length of the period of wakefulness preceding the time the user fell asleep, the sleep cycles that have passed, and the probable quality of the user's following wakeful state.

To determine a sleep cycle, the one skilled in the art is inclined to use a detector of eye movements because the only sleep cycle that shows visible characteristics is paradoxical sleep, and only that sleep cycle is characterized by eye movements. Incidentally, paradoxical sleep is also known in other literature as "rapid eye movement" sleep, or REM sleep, and in French "phase de mouvements oculaires," or PMO.

For example, the documents FR 2 597 995 and FR 2 634 913 present a device designed to awaken a user, and uses electrodes implanted in the eye region to detect eye movements. This device is not applicable because there is a risk of accidents linked to the electrodes by the eyes, and the electrodes disturb the user's sleep. Besides, the use of conductive gel, necessary for the electrodes to function properly, is at the same time disagreeable, dangerous, and bothersome. Furthermore, this document does not indicate any implementation of the electrode device to intake the electrical signals of the eye muscles, nor to process these signals or any necessary information regarding the sleep of the user that would allow for the detection of the onset of paradoxical sleep, nor to select a time to awaken corresponding to the beginning of a sleep cycle. Finally, the device described in this document cannot resolve the problem that it claims to solve, because the duration of paradoxical sleep, during which eye movements are apparent, are neither equal nor regular through the course of different sleep cycles. The duration of paradoxical sleep varies from one tenth to one third the length of the duration of the complete sleep cycle. The assumption that paradoxical sleep begins after a delay of one fourth to one fifth of the complete sleep cycle and that is has a predetermined duration does not therefore allow the beginning of the steep cycle to be accurately determined.

More generally, all information intake systems that obtain information about sensory activity, particularly those placed on the user's eyes, impose an annoyance that hinders activity and rest. In effect, the user's senses serve to awaken the user's attention and to give the central nervous system information to be processed. Furthermore, with the exception of the sense of touch, the sensory zones are concentrated on the face and are supported by a large density of tactile nerve endings and particularly sensitive protective reflexes. Any attempt to obtain information regarding sensory activity, such as eye muscle activity, causes a reduction in the user's concentration and/or the user's ability to rest.

SUMMARY OF THE INVENTION

The present invention intends to resolve these inconveniences.

According to a primary aspect, the present invention envisions a device that allows a user to know certain information, characterized in that it includes:

an information intake system that obtains a value that represents non-sensory biological activity of the user's body;

a means of filtration for the value obtained by the said information intake system, designed to provide a relative position of the said value within the cycle representing a temporal variation of the non-sensory biological activity, the said cycle being of a duration longer than one minute, and a means for the user to know the information representing the said relative position.

It should be observed that the.information intake system can possess a great number of different structures, all with the goal of obtaining information from, for example, sounds (blood flow, breathing, rubbing of the fabric of a sheet or clothing), thermal data (body temperature, expelled air), electrical data (conductivity at the skin surface, brain activity, nerve or muscle activity), pressure data (blood pressure, speed of expelled air, pressure of the body onto a pillow or a bed), movements, rubbings, electromagnetic waves, gaseous compositions, electrical conductivity, or respiratory or cardiac rhythms.

It should also be observed that the means of filtration can possess a number of structures, for example:

mechanical, for example similar to systems that incorporate tension by a spring in an "automatic" watch, but equipped with an absorber to reduce this tension with an absorber time constant less than the duration of the cycle, or electronic, for example by frequency filtration, by auto correlation, by correlation with a predetermined function, for example a sine function, or by Fourier transforms.

Finally, the implementation itself can also take on numerous structures; for example, a display on a watch that would permanently display the relative position in the cycle, and or the time of the beginning of the cycle, and/or the time of the end of the cycle; an auditory, visual, or vibratory alarm that would set off when a predetermined relative position in a predetermined cycle was reached; or by the turning on of a source of light.

According to these particular characteristics, the means of filtration is designed to integrate a difference between an obtained value and a predetermined value, (for example, the average of the obtained value during at least one cycle) and to provide the relative position of the said integral in the form of the relative position of the said integral within a range of values.

Because of these features, the user can determine if a biological resource is still available, or if his potential to perform is at its greatest, or if it will be at its greatest at a future point in a cycle.

According to other particular characteristics, the means of filtration is designed to integrate the said difference by applying a weighting function representing an elapsed duration.

Because of these features, the value of the integral principally represents the last obtained values.

According to other particular characteristics, the information intake system is designed to obtain a value representing a user's nonsensory biological activity, without bilateral contact with the human body.

Because of these features, the user's body is free to move with at least one degree of freedom. For example, the information intake system can obtain information from a distance, and can obtain values without contact with the human body (for example a motion detector or surveillance equipment) or can obtain information by having pressure applied to it by at least one part of the user's body (for example a pillow, a sheet, a chair, or a keyboard).

According to other particular characteristics, the information intake system is designed to obtain values representing the cardiovascular activity of the user.

Because of these features, the information intake device is easy to produce and of little cost, since it's conception and production can benefit from current knowledge in the field of tensiometers and/or pulse takers.

According to other particular characteristics, the said information intake system is designed to be used in a permanent relationship with the user's body.

Because of these features, the implementation of the present invention is discreet, non handicapping, and allows the user to have the freedom of movement to which he is accustomed and does not alter his capacity to concentrate, rest, or perform.

According to other particular characteristics:
the information intake system is designed to obtain a value once it is in its predetermined relationship with the user's body,
the means of filtration includes:
a memory for values obtained by the said information intake system,
a means to estimate the said values when the information intake system is not in the predetermined relationship with the user's body,
a means of implementation designed to put the said estimation to the user's use.

Because of these features, the information to be put to use is representative of either a relative position determined as a function of the obtained values, or as a function of an estimation, that can, advantageously, be based on the preceding obtained value obtained when the information intake system was in the predetermined relationship with the user's body.

Thus, for example, if the information intake system is worn on the wrist, it has a relative position to be used during a cycle, for example a sleep cycle, when the user is not actually wearing the said information intake system on the wrist.

According to other particular characteristics, the device as it is succinctly described herein includes a memory of a predetermined position in the said cycle and the implementation of the said information concerning the relative position is designed to produce a signal when the said relative position is equal to the said predetermined position.

Because of these features, when the user wishes to begin an activity at a predetermined position in a cycle, for example to awaken at the end of a paradoxical sleep cycle, he is made aware by the implementation of the impending arrival of this predetermined position.

According to other particular characteristics, the means of implementation of the said information concerning the relative position is designed to permanently have the said relative position available to the user.

Because of these features, the user can always consult the implementation to inform himself of his instantaneous relative position.

According to other particular characteristics, the means of filtration is furthermore designed to determine the duration of the cycle. Because of these features, the duration of the user's cycle is taken into account in determining the position in the cycle, rather than a predetermined duration. Therefore, if the user disturbs his cycle, for example at the end of an airplane trip or a surgical operation, the duration of the cycle is adjusted by the means of filtration to take into account this disturbance.

According to particular characteristics, the means of filtration includes a means of processing designed to effectuate a frequency analysis of the obtained value.

Because of these features, the noise that affects the value obtained by the information intake system is eliminated since its frequency is sufficiently different from the frequency of the cycle. The reader will advantageously refer to the general knowledge of a person skilled in the art of processing signals to determine the meaning of the word "sufficiently" in the preceding phrase.

According to particular characteristics, the information intake system that obtains a value representing a non-sensory biological activity of the user's body is designed to obtain a value from a number of biological events, and the means of filtration is designed to determine a duration of a cycle at least ten times greater than the average duration between two events obtained by the information intake system.

Because of these features, repetitive events, such as the heart beating, the lungs breathing, the limbs or head moving, advocate the use of relative positions in cycles of a duration greater than a few tens of seconds.

According to other particular characteristics, the means of filtration is designed to cause a recurrent processing over several periods to measure the variation of the duration of the said cycle.

Because of these features, the present invention can be easily put to use for biological cycles of which the duration is not constant but progressively evolves.

According to other particular characteristics, the information intake system is designed to provide a value that represents the muscular activity from at least one of the user's limbs.

Because of these features, the information intake device is easy to produce and of little cost, since it's conception and production can benefit from current knowledge in the field of pedometers, actimeters, actigraphs, and accelerometers.

According to other particular characteristics, the information intake system is designed to provide a value that represents the electrical activity in the user's body without bilateral contact with the user's head.

Because of these features, the electrical brain, nerve, or muscle waves, which represent internal activity of the human body, can be taken into account by the means of filtration.

According to other particular characteristics, the information intake system is designed to provide a duration separating two keystrokes on a computer keyboard.

Because of these features, the rapidity of the keystrokes can be taken into account by the means of filtration and the implementation of the present invention can be activated by the execution of a program by a microprocessor or a computer.

According to other particular characteristics, the information intake system is designed to be positioned at a distance from the user's body and to provide representative information regarding the movements of the said body.

Because of these features, the freedom of movement of the body is not at all reduced and none of the senses detects the presence of the information intake system, not even the sense of touch.

According to other particular characteristics, the means of filtration is designed to implement a detection of the difference between the obtained value and an average of obtained values corresponding to the same relative position in the cycle.

Because of these features, the user has, for his use, information about a biological activity. The user can benefit from this information, for example, during training, for example in typing, in physical exercise, in cardiac activity, or in the field of electrical cerebral wave emission.

According to other particular characteristics, the means of filtration is designed to effectuate an integration of the said difference and a means of using a value that represents the result of the said integration.

Because of these features, the user can, for example, use the integration of the value over an entire cycle, to eliminate the cyclical fluctuations in the considered value.

According to other particular characteristics, the means of implementation includes a memory of values, each corresponding to a relative position, and is designed to display, for each relative position, the corresponding value of the relative position provided by the means of filtration.

Because of these features, whenever a relative position in the memory corresponds to:
- a prompting, for example to relax, or, to the contrary, to make intense effort,
- a feeling, for example of well being, or of agility,
- a high or low ability to perform, for example intellectually, emotionally, or physically, this prompting, feeling, and/or ability to perform is or are to be made known to the user.

According to other particular characteristics, the device described by the present invention includes a memory of a duration of a cycle, and the means of filtration is designed to determine a duration of a cycle and to compare the determined duration of the cycle to the duration stored in the memory, and when the duration is greater than the duration stored in the memory, to determine the relative position in comparison to the duration stored in memory or to the previous duration of the cycle determined by the means of filtration.

Because of these features, when the obtained value is disturbed, to the point where the means of filtration produces an evaluation of the duration of the cycle that is very different from the predetermined value for that particular situation, it is the estimated duration of the cycle that is used as the standard for the relative positions.

According to other particular characteristics, the means of implementation includes:
- a memory designed to store, on one hand, a number of sleep cycles, and, on the other hand, a relative position in a cycle, and
- a means to cause the emission of light rays towards the user's eyes, and
- is designed to begin the emission of light rays when, on one hand, the number of sleep cycles stored in the memory have been attained, and, on the other hand, when the relative position provided by the means of filtration is equal to the relative position stored in the memory.

Because of these features, the present invention can be applied to an alarm clock which would allow a user to be awakened at a favorable moment in his or her sleep cycle, without having to wear an information intake system that would disturb his or her sleep.

According to other particular characteristics, the means of implementation includes a memory designed to store a predetermined relative position and is designed to display the time at which the said relative position stored in memory will occur.

According to other particular characteristics, the means of filtration is designed to detect the impending arrival of the "reference" relative position in the cycle, and to locate the other relative positions in relation to the previous arrival of the reference relative position.

Because of these features, whenever a relative position is easy to determine, for example like an awakening at the end of a circadian cycle, the other positions are located in relation to this relative position.

According to other particular characteristics, the means of filtration is designed to determine the end of a phase of paradoxical sleep in the sleep cycle.

Because of these features, the best moment to awaken the user is determined to be following the end of a phase of paradoxical sleep.

According to other particular characteristics, the means of filtration is designed to:
- test a first value of the duration of the cycle, or period, by detecting cycles of variations of the said value, for example by autocorrelation or by correlation with a sinusoidal function over one sinusoid, and
- if the number of detected cycles, during a reference duration given by taking into account the said period, is greater than the ratio of the reference duration over the said period, test a new duration of a shorter cycle,
- if the number of detected cycles, during a reference duration given by taking into account the said period, is less than the ratio of the reference duration over the said period, test a new duration of a longer cycle, and so forth until the number of detected cycles is equal to the said ratio.

Because of these features, a recurrence allows the average duration of the cycle in the given reference duration (for example, a duration of wakefulness) to be determined.

According to other particular characteristics, the information intake system is incorporated in an object that has a permanent function other than that of obtaining the said values representing a non-sensory biological activity of a user's body, such as jewelry, a watch, a pillow, a bed, a presence detector, a motion detector, an article of clothing, glasses, or headphones.

Because of these features, the user is not bothered by the interaction that his body has with the device described by the present invention.

According to a second aspect, the present invention envisions a method to allow the user to know information, including:
- a step of obtaining a value representing a non-sensory biological activity of the user's body,
- a step of filtering the obtained value along with the step of obtaining the value to provide a relative position of the said value in a cycle representing a temporal variation of the said non-sensory biological activity, the said cycle being of duration greater than one minute, and
- a step of allowing the user to know the information representing the said relative position.

Because of certain features of the present invention, the user is informed of the preferred time to begin or interrupt a period of sleep. He can also, according to particular embodiments of the present invention, choose the best time to go to sleep or be awakened.

According to particular characteristics, at least one physiological information intake system is designed to detect a parameter of the functioning of the cardiovascular system.

Thus, the variations of cardiac rhythm or arterial pressure, or any arrhythmias can be used to detect a period of extreme activity.

According to particular characteristics, at least one physiological information intake system is designed to detect a parameter of the functioning of the respiratory system.

Thus, the variations of respiratory rhythm, respiratory flux, the chemical composition of the expelled gases, and the regularity of the respiration can be used to detect a period of extreme activity.

According to particular characteristics, at least one physiological information intake system is designed to detect a parameter of the functioning of electrical cerebral waves.

Thus, the electrical cerebral waves can be used to detect a period of extreme activity, particularly during a period of sleep.

According to particular characteristics, at least one physiological information intake system is designed to detect a parameter of the functioning of the muscular system.

Thus, the electrical muscular activity and the movements of the body can be used to detect a period of extreme activity, particularly during a period of sleep.

According to preferred characteristics, all information intake systems in contact with the user's body are in dry contact with the user's body. Thus, the user is not bothered by any liquid or any gel.

According to another aspect, the invention envisions a time-keeping article, such as a watch or an alarm clock, that would incorporate at least one part of a device as it is succinctly described herein.

According to another aspect, the present invention envisions a pillow that would incorporate at least one part of a device as it is succinctly described herein.

According to another aspect, the present invention envisions a memory, removable or not, capable of being read by an information system or by a microprocessor, and of storing information containing instructions for a program for processing information, to implement the device or the method described herein.

The inventor has also discovered that the users of watches and clocks, including clocks that are part of a computer, would be interested in knowing the instantaneous values of their different physical or psychological capacities (their speed of inquiry, their speed of reasoning, their alertness, their dexterity, their overall vigor, their overall feeling (of well being), their concentration of melatonin (the feeling that they need to sleep)) that correspond to a particular moment in the day or in a biological cycle.

To this effect, the present invention envisions, according to another aspect, a device that displays variable parameters of a regular cycle, including a memory that stores the values of each of these parameters, a clock that provides the time, a means to correlate the time provided by the clock with at least one value of these parameters, and a means to display at least one value that has been correlated with the time provided by the clock.

The present invention also envisions a combination of this last aspect with each of the other aspects of the invention, as have been described herein, a combination in which the clock is replaced by the relative position in a cycle, this relative position being correlated with at least one value of a parameter displayed by the means of display.

BRIEF DESCRIPTION OF THE DRAWINGS

Other advantages, goals, and characteristics of the invention will surface in the description that will follow in the attached drawings in which.

DETAILED DESCRIPTION OF THE INVENTION

Figure 1A:
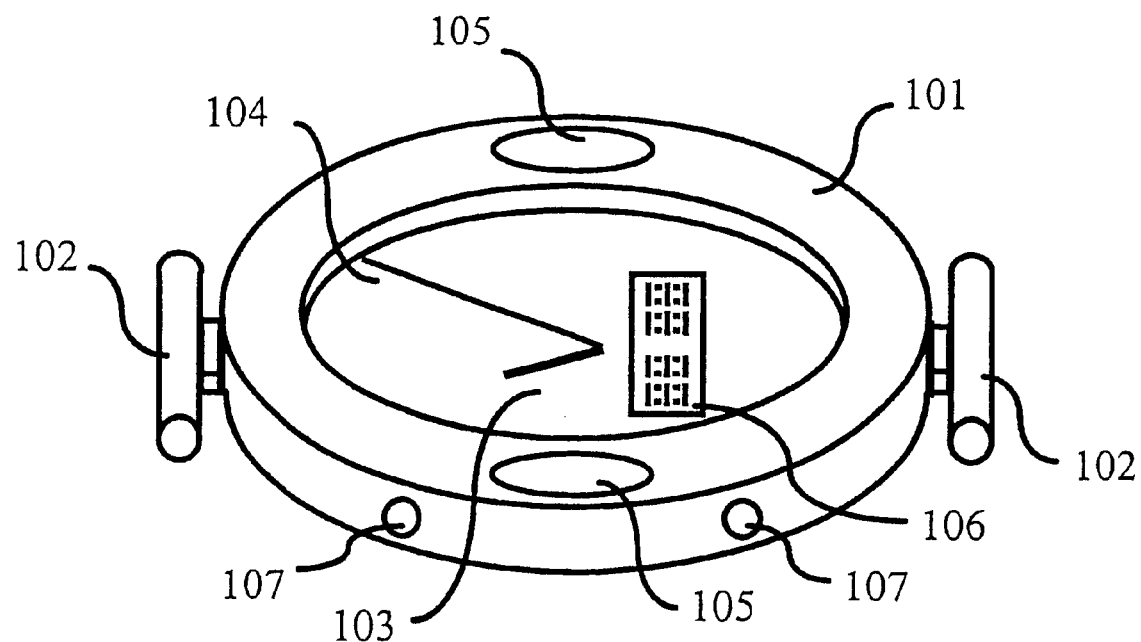
FIGS. 1A and 1B represent views from above and below, respectively, in perspective, of a first embodiment of the device described by the present invention, incorporated in a watch.
Figure 1B:
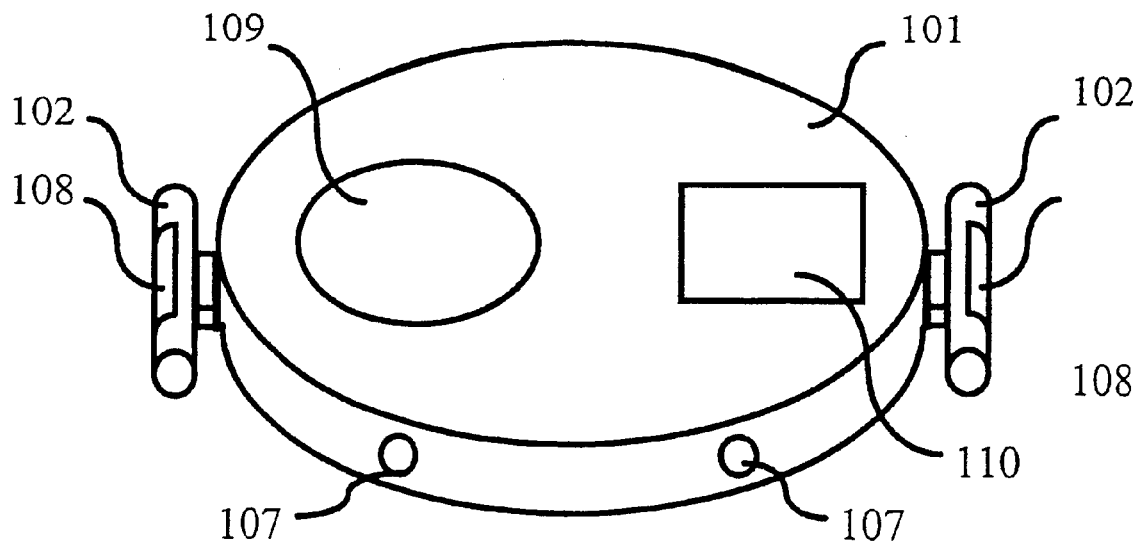
Figure 2:
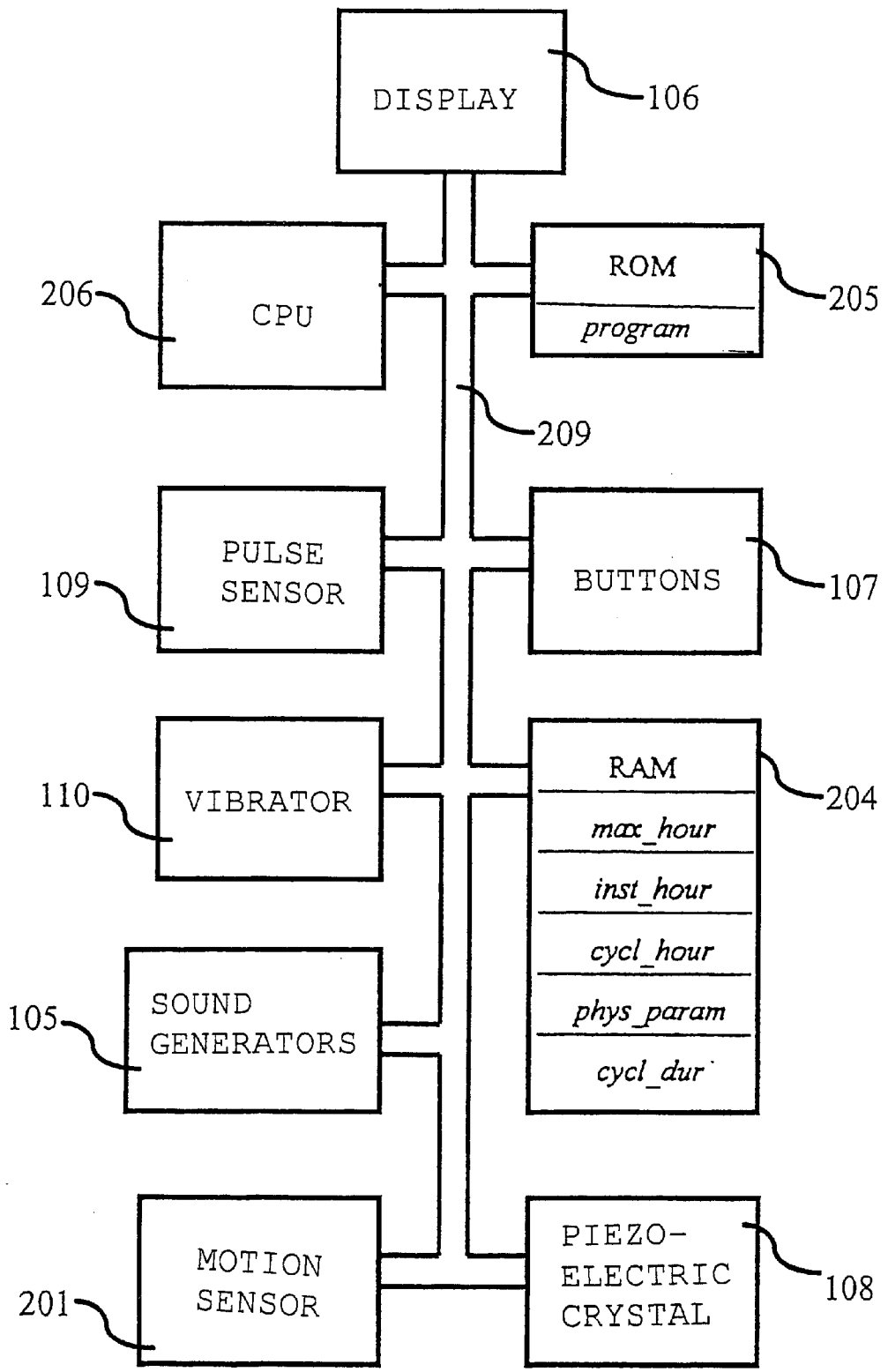
FIG. 2 represents a schematic electronic circuit incorporated in the device illustrated in FIG. 1.
Figure 3:
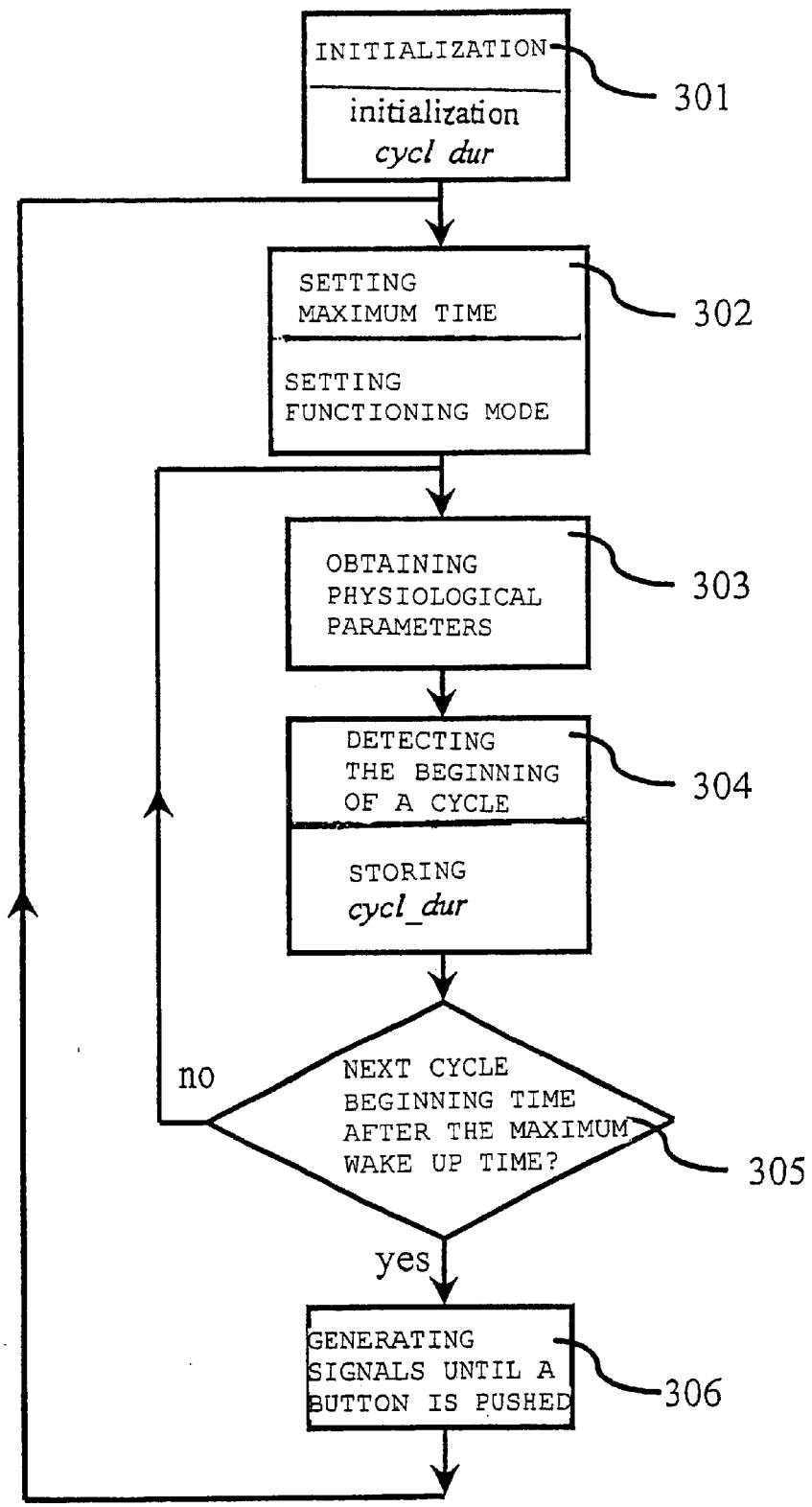
FIG. 3 represents a flow chart of the electronic circuit illustrated in FIG. 2.

The first embodiment described and shown by FIGS. 1 to 3, concerns a device incorporated in a watch designed to awaken the user at the end of a sleep cycle.

FIG. 1A shows the watch casing 101, of a known type, connected, by watch band attachments 102, to a watch band (not shown). The watch band attachments 102 are designed to unite the ends of an elastic watch band and the casing 101. The casing 101 includes a mechanism that puts in motion, in the classical way, an hour hand 103 and a minute hand 104 in such a manner that the two hands together indicate the current time on the watch dial. Two sound generators (or electro-acoustic transducers) 105, of known type in the field of electronic watches and electronic games, are designed to emit sounds audible to the user, during his sleep.

They are found on the top face of the casing 101 (FIG. 1A), on either side of the watch dial.

A display 106, placed here on the watch dial, is designed to display alphanumeric symbols to represent the time (hour and minutes) of the optimum wake up time or instructions on the functioning and programming of the watch. The display 106 is well known in the field of digital display watches, and can be, for example, of liquid crystals. Four buttons 107 are placed on the peripheral edge of the watch casing, in a manner known in the field of electronic watches.

It should be observed that a pulse sensor 109 and a vibrator (or electromechanical transducer) 110 are located on the bottom face of the casing 101 (FIG. 1B), and that a piezoelectric sensor 108 is located in each of the watch band attachments 102.

The casing 101 includes an electronic circuit of filtration illustrated in FIG. 2, that receives electric signals from the sensors 108 and 109 and from the buttons 107 and emits electric signals to be received by the display 106, the electro-acoustic transducers 105 and the vibrator 110 (in order to allow the user to know information representing a relative position, or phase, in a biological cycle).

The circuit is organized around a bus 209 and includes, connected to this bus, the display driver 106, the central processing unit (CPU) 206, the read only memory (ROM) 205, the random access memory (RAM) 204, the buttons 107, the pulse sensor 109, the vibrator 110, the electro-acoustic transducers 105, the motion sensor 201, and the piezoelectric crystals 108.

The bus 209 is made of electric lines. It transports the signals from a clock (not depicted) to synchronize the functioning of all the electrical components. The central processing unit 206, the read only memory 205, and the random access memory 204 are preferably incorporated in a unique integrated circuit, called a microcontroller. To facilitate the explanation, they are considered separate in the description of FIG. 2. Either way, the means and functions permit the current time to be displayed, by way of the hands 103 and 104, which are not depicted here, as they are well known in those skilled in the art of clocks.

The buttons 107 allow the user to set his or her watch to the correct time, to choose a mode of operation, to choose an optimum time to be awakened (see FIG. 3) or to choose a number of cycles, according to known techniques.

The pulse sensor 109 is designed to detect at least half of the user's heartbeats.

In a first variation, the pulse sensor 109 is a radial motion sensor, in relation to the axis of the arm that wears the watch in the first embodiment of the invention (that is vertical movements, in FIGS. 1A and 1B). It therefore includes a sensor of motion or acceleration, for example a piezoelectric crystal.

In a second variation, the pulse sensor 109 is a sound sensor that detects sounds caused by the flow of blood in the blood vessels near the watch. These sounds can also be infrasonic (of the order of 1 Hertz) since this frequency corresponds to cardiac rhythms at rest, sonic, or ultrasonic, since the flow of blood in the blood vessels causes sound waves.

In a third variation, the pulse sensor 109 is an electric sensor designed to detect electrical signals emitted at each heartbeat, according to techniques known in electrocardiography or in the cardiac surveillance systems used in sports equipment (stationary bicycles, treadmills, etc). Furthermore, this sensor is designed to sense the electrical activity of the muscles or of the brain. These three electrical activities (cardiac, muscular, and cerebral) present the same general variations throughout the course of sleep cycles.

In a fourth variation, the pulse sensor 109 receives signals from the piezoelectric crystals 108 that represent the tension in the elastic band that encircles the wrist wearing the watch. In this variation, the user must ensure that the watch band is snug around the wrist when he or she first puts on the watch.

In a fifth variation, the pulse sensor 109 is a thermal sensor that obtains the temperature of the blood in at least one blood vessel in the wrist. For the implementation of this fifth variation, one skilled in the art can refer to "CASIO" watches that include an "exercise pulse monitor" with a thermal sensor on the back face and a liquid crystal display designed to display the pulse.

In a sixth variation, the pulse sensor 109 is identical to known tension meters worn on the wrist.

In all cases, the pulse sensor extracts, from the signals that it receives, the bass frequency signals (of the order of a hertz) that correspond to cardiac pulses, and transmits a signal to the central processing unit 206 at each detection of a cardiac pulse. The central processing unit analyzes the pulsation signals received from the pulse sensor 109 and processes them to, on one hand, eliminate parasitic signals (due, for example, to movements of the user), and on the other hand, to restore the missing signals (signals too weak to have been detected). This processing is effectuated by taking into account the number of signals from the clock that separated the signals of cardiac pulses and the fact that cardiac pulses are generally regular, that is that the pauses between successive cardiac pulses do not vary more than fifty percent.

This processing is known to those skilled in the art of the extraction and reconstitution of signals in a range of known frequencies, from a set of signals.

The motion sensor 201 is designed to detect the movement of the user's wrist. It can include the pulse sensor depicted herein, where the signals represent movements, but these signals must be processed taking into account the fact that movements cause very intense parasitic signals and are not very regular in comparison to cardiac signals. The motion sensor 201 can also include piezoelectric crystals known in the field of accelerometers.

According to one variation, the motion sensor 201 is similar to motion sensors in actimeters or actigraphs.

Also, the piezoelectric crystals 108 would permit the inclusion of an arterial pressure sensor, since the tension of the signal coming from these crystals represents the tension of the elastic watch band of the watch.

The vibrator 110 is of a known type in the field of mobile telephones and radio wave message receptors known as "pagers." It is designed to emit a vibration perceptible to the user, when the vibrator is in contact with the user's skin, in response to an alternate signal of command.

It should be observed that the pulse sensor 109, the motion sensor, and the arterial pressure sensor can be confused and use different parameters of the same signals (sonic, electric, dynamic).

If we refer to the book "le sommeil et le rêve," ["sleeping and dreaming"] by M. Pierre MAGIN, published by Presses Universitaires de France, the following can be learned:

"the time it takes to fall asleep can vary from a few minutes to a few hours. The [paradoxical] sleep begins, in general, after 1 hour and 30 minutes of true sleep. As the night progresses, the duration of profound sleep cycles decrease while the duration of [paradoxical sleep] cycles increase. In effect, the succession of the [paradoxical sleep] cycles and the [profound sleep] cycles develops following a variable rhythm period. The longest [profound sleep] cycle interferes before the first cycle of [paradoxical sleep]" (p. 38), and "When the cycles of [paradoxical sleep] near the awakening time, a synergy of manifestations can be observed; the temperature rises ( . . . ) and respiration and cardiac activity accelerates" (p. 57).

"The [paradoxical sleep] is in fact a very profound sleep. While it is occurring, the subject is practically oblivious to all stimuli designed to awaken. The interruption of this cycle is damaging to the overall quality of sleep and to the health" (p. 95).

Thus, according to the invention, whenever it is applied to the management of sleep by controlling the time of awakening, the attempt to awaken the sleeping user will be made according to the two following constraints:

on one hand, before the maximum wake up time that the user has selected, by way of the buttons 107 and the display 106, and on the other hand, at the beginning of a sleep cycle; that is, at the end of a paradoxical sleep cycle.

To this effect, the central processing unit 206 implements the software represented by the simplified flow chart illustrated in FIG. 3.

The read only memory 204 stores the instructions of this program, in the buffer "program," as well as the constants implemented by this program.

The random access memory 205 stores the following values in entries that, for convenience, have the same names as the variables:

the value of the maximum wake up time, in the buffer "max_hour";

the value of the instantaneous time, in the buffer "inst_hour";

the values of the times when the sleep cycles began, in the buffer "cycl_hours";

the values of the durations of the five last sleep cycles, in the buffer "cycl_dur"; and the values of the averages of physiological parameters, over a period of a few minutes, in the buffer "phys_param."

It should be observed here that the considered entries in the memory could just as well be limited to binary information, or they could have sufficient capacity to store a table of a few thousand values, for each physiological parameter.

FIG. 3 shows an operation 301 to initialize the device, and, in particular, the functions of a classic watch (to set up the year, month, day, hour, minute, and instantaneous second), according to known techniques which the user utilizes to implement the buttons 107, the display 106, and the watch hands 103 and 104.

The operation 301 follows the placing of batteries in the watch. During the operation 301, the entries of the random access memory 204 are all initialized to zero, with the exception of the buffer "inst_hour" which permanently contains the instantaneous time.

During the operation 301, the user is prompted to provide the duration of his sleep cycles, if he knows it. The value of this duration is stored in the memory in the buffer "cycl_dur." The buffer "cycl_dur" functions according to the principle of "first in, first out" and only stores the five most recent values entered. The default duration of the user's sleep cycle is considered to be equivalent to 80 minutes.

Next, during the operation 302, the user chooses a maximum time to be awakened; that is, the time at which he or she wants to be sure to be awake. To this effect, the user utilizes the buttons 107 and the display 106, according to techniques known in the programming of watches that possess alarm functions. If the wake up time will not allow the completion of a sleep cycle; that is, when the difference between the instantaneous time, stored in the buffer "inst_hour," and the maximum wake up time, stored in the buffer "max_hour," is less than the value stored in the buffer "cycl_dur," the user is informed that he'll be awakened at the maximum wake up time, by the vibrator 110 and the display 106. In this case, the watch functions exactly as existing watches with alarms.

If not, the user is told by the device that, if the device is to function as designed, he or she must go to sleep immediately, and, still in the course of operation 302, the device then analyzes each parameter to determine the moment the user falls asleep. For example, sleep is detected when the average pulse rate slows over sixty successive minutes by twelve percent when compared to the sixty preceding minutes, and/or when the average number of movements over sixty minutes falls by at least ninety percent when compared to the sixty preceding minutes and/or when the arterial pressure falls, with the same restrictions, by five percent. The durations to be analyzed and the variation rates used for each parameter could be adjusted by the analyzing of temporal functions of the parameter values.

The beginning of a reference duration is characterized by the beginning of the period of 60 minutes that corresponds to the time the user fell asleep, and if the device did not detect a falling asleep time during the first two hours after the beginning of operation 302, the beginning shall be, by default, the beginning of operation 302.

Throughout the operation 303, the central processing unit 206 receives signals from the pulse taker 109, the arterial pressure sensor 108, and the motion sensor 201, and processes them to:

eliminate parasitic signals, restore missing signals, determine a value for each physiological parameter, averaged over each minute of the night.

For each of the physiological parameters (in this case the pulse, the arterial pressure, and the muscular activity of the arm wearing the device), the central processing unit 206 places the results of these processings in the buffer "phys_param" at the end of each minute. To this effect, the buffer "phys_pararn" functions as a "first in, first out" memory and stores only values corresponding to the ten most recent hours.

Throughout the operation 304, the central processing unit 206 determines the end of a cycle, that is the end of a period of wakefulness or a period of paradoxical sleep, by determining the coming of a phase of decreased frequency of heartbeats, a phase of decreased arterial pressure, and a phase of decreased muscular movements.

To this effect, the central processing unit 206 effectuates a filtration and a determination of the duration of the cycle in the following manner:

the central processing unit 206 tests a first value of the cycle duration, or period, equal to the cycle duration stored in the buffer "cycle_dur," by effectuating the product of the resulting function, for each parameter, with a same sinusoid, and by repeating the operation as long as the considered duration is found within the current reference duration, from the beginning of this duration, defined during the operation 302, to the time at which the considered operation 304 is effectuated, and if the number of cycles detected over the resulting temporal function, during the reference duration, is greater than the ratio of the reference duration over the duration of the tested cycle, the tested duration stored in the buffer "cycls_dur" is replaced by a new shorter cycle duration, for example one minute, if the number of cycles detected over the resulting temporal function, during the reference duration, is less than the ratio of the reference duration over the duration of the tested cycle, the tested duration stored in the buffer "cycle_dur" is replaced by a new longer cycle duration, for example one minute.

These operations repeat until the number of cycles detected is equal to the said ratio, with a precision of one minute over the duration of the cycle.

According to a variation, the central processing unit 206 determines the duration of a cycle by effectuating an autocorrelation over the temporal function representing each analyzed parameter, by taking into account all the possible cycle durations, minute by minute, from sixty to one hundred minutes, and by using this duration to shift the autocorrelation, by eventually repeating this autocorrelation as many times as the studied cycle occurs in the reference period, and by determining the duration of the cycle by presenting the greatest factor of autocorrelation, according to techniques known in the field of signal analysis.

If the cycle duration is computed by using an autocorrelation, the beginning of the sleep cycle is considered to be one sixth of a cycle before the position, in a cycle, for which, after a maximum of the average over a duration equal to one third of a cycle, the autocorrelation function presents, for the first time, an average, over one third of the cycle, equal to the average over the whole cycle.

If the cycle duration is computed by using one or more sinusoid (each sinusoid beginning at zero, then becoming positive, then negative, then returning to zero), the beginning of the sleep cycle is considered to be one sixth of a cycle before the position, in a cycle, for which, after a maximum of the average over a duration equal to one third of a cycle, the correlating function presents, for the first time, an average, over one third of the cycle, equal to the average over the whole cycle.

If a cycle is not detected, the central processing unit 206 analyzes the values of the physiological parameters and determines that a paradoxical sleep cycle has occurred when, after at least two of the physiological parameter values have become greater than the average value of these parameters, taken over the preceding 110 minutes, and this over a duration D1 of at least ten minutes (paradoxical sleep), at least two of the physiological parameter values have become less than the average of these same parameters, taken over the last period of twice the duration D1, and this over a duration D2 greater than five minutes (light or heavy sleep). For example, the table included herein, that presents in succession the values of the physiological parameters averaged over the 110 last minutes and the values measured during one minute, corresponds to a paradoxical sleep cycle followed by six minutes of light or heavy sleep.

| Pulse | Arterial Pressure | Movements | Detected Cycle |
|---|---|---|---|
| Averages from the 110 last minutes: | | | |
| 56 | 10 | 4 | D2 |
| Successive values for the following minutes: | | | |
| 55 | 10 | 1 | D2 |
| 55 | 10 | 2 | D2 |
| 57 | 10 | 1 | D2 |
| 58 | 10 | 3 | D2 |
| 60 | 10.5 | 5 | D1 |
| 62 | 10.5 | 7 | D1 |
| 65 | 10.5 | 4 | D1 |
| 65 | 11 | 6 | D1 |
| 70 | 11 | 12 | D1 |
| 63 | 11 | 15 | D1 |
| 66 | 11 | 10 | D1 |
| 60 | 10 | 3 | X |
| 58 | 10 | 8 | D2 |
| 55 | 10 | 2 | D2 |
| 55 | 10.5 | 2 | D2 |
| 54 | 10 | 2 | D2 |
| 55 | 10 | 2 | D2 |
| 56 | 10 | 2 | D2 |

In this previous case, since a cycle was not detected, by correlation or by autocorrelation, throughout the course of operation 304, the central processing unit 206 effectuates, in order:

the detection of when each average value of a physiological parameter from the previous minute (the value stored in the buffer "phys_param") is greater than the average value from the 110 previous minutes (the value calculated from the values stored in the buffer "phys_param");

the counting of the number of minutes for which this occurs successively for at least two parameters;

if this number of minutes, D1, is greater than three minutes, the detection of when each average value of a physiological parameter, from twice D1 minutes, (the value calculated from the values stored in the buffer "phys_param"), is greater than the average value from the previous minute (the value stored in the buffer "phys_param");

the counting of the number of minutes for which this occurs successively for at least two parameters;

if this number of minutes, D2, is greater than five minutes, the storing of the time of the end of the cycle, the instantaneous time, in the buffer "cycl_hour."

The buffer "cycl_hour" functions as a "first in, first out" buffer, and therefore only stores the two most recent cycle beginning times.

At the end of operation 304, the central processing unit 206 adds the value of the most recent cycle duration to the buffer "cycl_dur."

For the test 305, the central processing unit determines whether or not the next cycle beginning time is after the maximum wake up time (stored in the buffer "max_hour" of the random access memory 204).

To this effect, the central processing unit 206 adds to the most recently detected cycle beginning time determined in the preceding operation 304, the average value of the non-zero values of the cycle durations, stored in the buffer "cycl_dur," and determines if the calculated sum is greater or less than the time stored in the buffer "max_hour."

If the result of test 305 is negative, the operations 303 and 304 are repeated. If the result of test 305 is positive, then during operation 306, the central processing unit 206 instructs the vibrator 110 to function, and, if the user does not awaken after a period of thirty seconds, the central processing unit 206 instructs the sound generators 105 to function, until the user pushes one of the buttons 107.

Next, the operations and test 302 to 306 are repeated.

The filtration circuit therefore processes the value obtained from each sensor and produces a relative position of the said value in a cycle representing a temporal variation of a non-sensory biological activity, the said cycle having a duration greater than one minute.

According to a variation, when the user is awakened by the device, that is at the moment he pushes the button 107, at the end of operation 306, the central processing unit 206 instructs the display 106 to display the next proposed wake up time, that is the projected end of the next cycle, if the user should decide to sleep more. If the user then decides to sleep more, the central processing unit 206 again instructs an awakening at the beginning of the next cycle.

Figure 4:
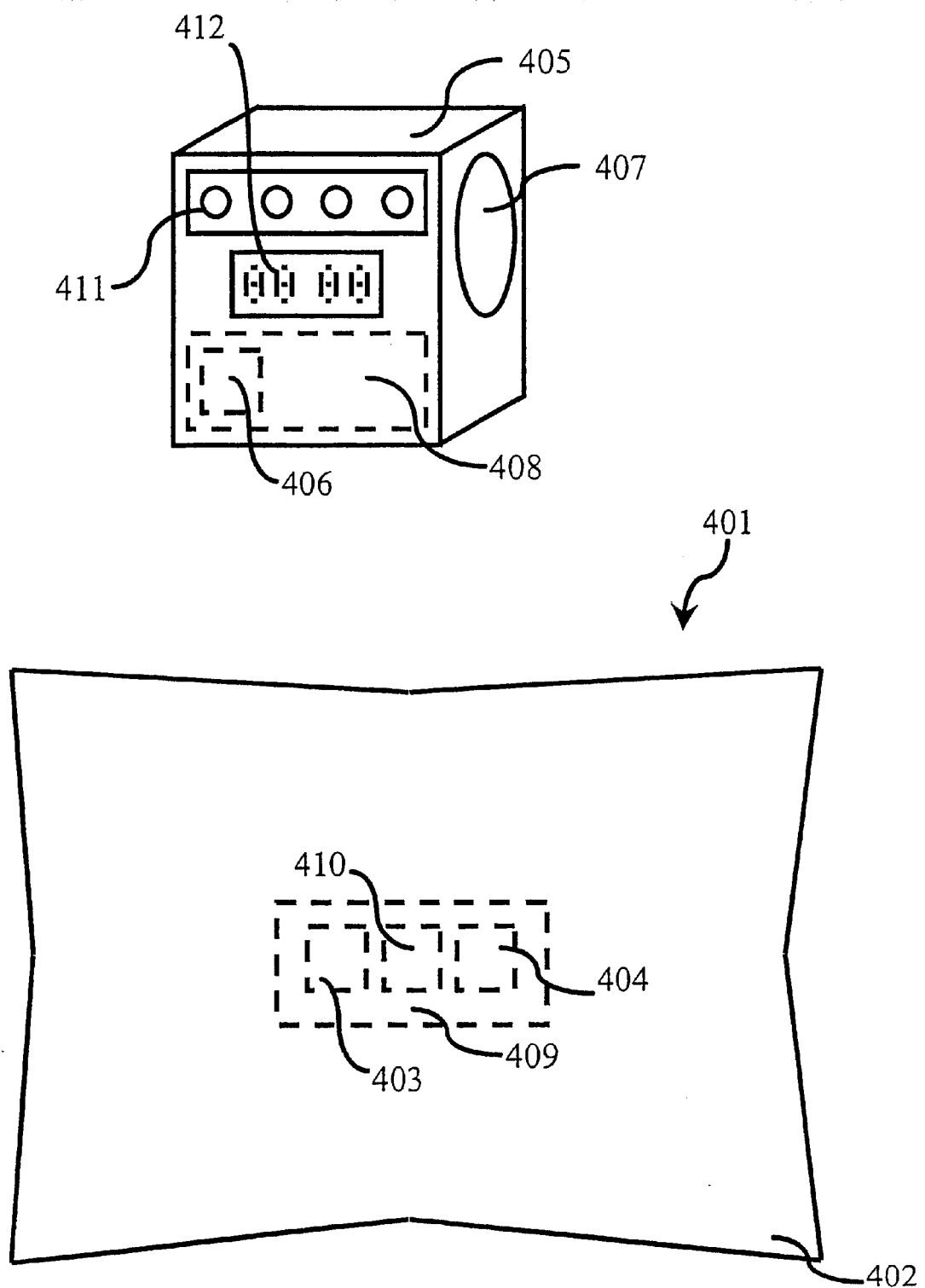
FIG. 4 represents a second embodiment of the device described in the present invention, incorporated in a pillow and in an alarm clock.

FIG. 4 depicts a pillow 401, covered by a pillowcase 402, including a sensor 403 of pressure exerted on the pillow, an electronic circuit 409 including an acoustic emitter 410 (to put information representing a relative position or phase in the sleep cycle to the use of the user) and an emitter/receptor 404. Also, an alarm clock 405 includes an emitter/receptor 406, an alarm 407, and an electronic circuit 408 for filtration.

The pillow 401 is a pneumatic pillow. The pressure sensor 403 is an acoustic microphone. For example, the microphone membrane separates a sealed chamber from the rest of the pillow. The emitter/receptor 404 is designed to emit a short range signal that the emitter/receptor 406, designed to receive signals, can detect, and vice versa. For example, the emitter is a radio wave emitter or an ultrasonic emitter.

The alarm clock 405 includes a keypad 411, a display 412, and at least one electro-acoustic transducer 407 designed to emit the wake up alarm. The circuit 408 is connected to all the electronic components of the alarm clock 405, and functions as the circuit in the first embodiment, receiving signals from the emitter/receptor 406. It returns the wake up signals first to circuit 409, which instructs the emission of sounds from the actual interior of the pillow, by the acoustic emitter 410, and then, after an initial waiting period, if the user does not push the alarm clock buttons, the circuit 408 instructs the alarm 407 to ring.

It should be observed that, in this second embodiment, the acoustic sensor allows for the obtaining of cardiac sonar frequencies, head movements, and respiratory movements.

One variation could include a pillow that is not pneumatic, and a sensor 403 that detects sound caused by the rubbing of the head and the arms on the pillowcase 402.

One variation could include a sensor of electric fields adjoined to an acoustic sensor 403, to detect electric waves emitted by the brain, during sleep, according to techniques known in the field of electroencephalograms, but with a higher sensitivity, and a pillowcase that conducts electric signals and is connected to an electric field sensor. These well known electric waves are processed, differentiated, and analyzed according to well known signal processing techniques and are not detailed here (one can refer to Pierre Magnin's book mentioned herein to better understand the details concerning different waves and their correspondence to different phases of sleep). In this non-depicted variation, the sensor is therefore designed to provide a value that represents an electrical activity of the user's body without bilateral contact with the user's head.

A non-depicted variation could include at least one of the mentioned sensors in FIG. 4 being inserted in the user's mattress, in a place where the user will sleep.

A non-depicted variation could include an electric wave sensor being inserted in the alarm clock and detecting the cerebral waves mentioned herein from a distance, without the sensor needing to be in contact with the user.

A non-depicted variation could include at least one sensor to measure the tension in the bed sheet or in the pillowcase.

In the same manner, the device in this invention is used for the management of bed and sleeping times, with daytime cycles being detected in the same manner as sleep cycles.

For each of these two first embodiments, the position in the cycle and the information about preferential beginning or end of periods of activity are displayed on the display, in the form of a percentage of the cycle gone by and a relative position in the cycle, and the passing of the beginning and middle of each cycle causes an emission of a sound and/or vibratory signal.

Figure 5:
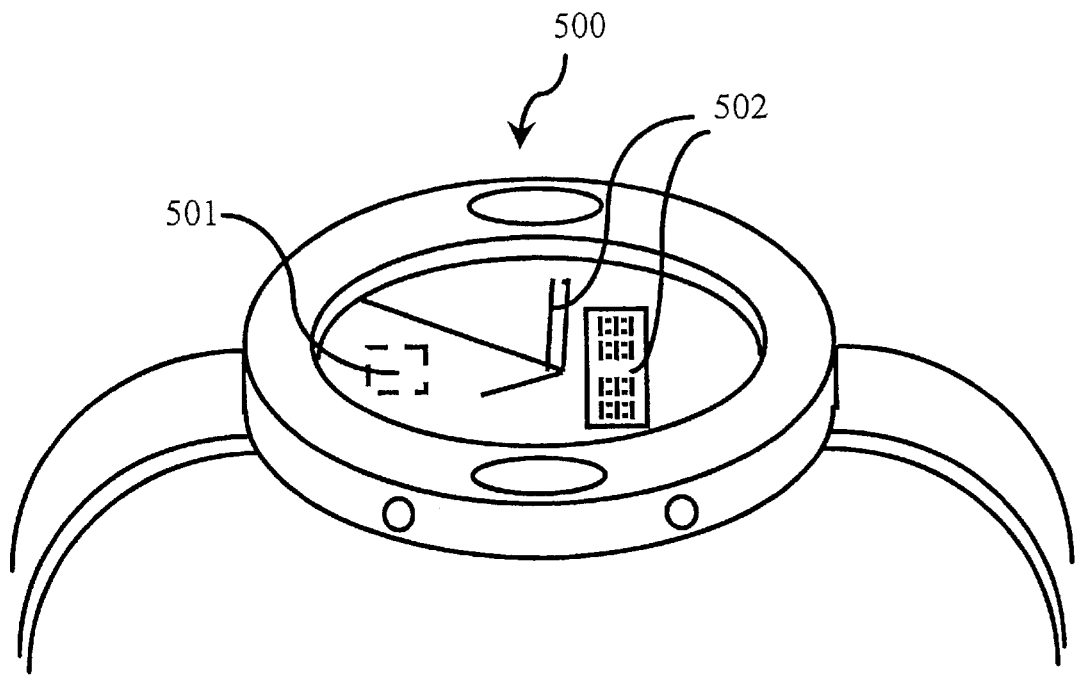
FIG. 5 represents a view from above, in perspective, of a third embodiment of the device described by the present invention, incorporated in a watch.

FIG. 5 represents a view from above, in perspective, of a third embodiment of the device of the present invention, incorporated in a watch. This embodiment of the present invention includes all the elements of a tension meter 500 designed to be permanently worn on a wrist, and to which has been added a memory 501 that stores a program for the functioning of the device and a means of displaying the relative position in the biological cycle 502, including here, on one hand, an alphanumeric display for four characters (or digits) and, on the other hand, a supplementary partially transparent watch hand.

Two programs are added to the memory, besides the ones that allow for the functioning of the traditional watch. The first program controls the measuring of the pulse and/or the arterial pressure, at regular time intervals, for example four times per minute. This program writes the results of these measurements to the random access memory.

The second program is a program that performs a frequency analysis on the variations in the pulse and/or the arterial pressure (high, medium, or low) designed to detect periods of variation in pulse and/or arterial pressure greater than one minute and less than twelve hours. Preferably, this program detects periods between ten and two hundred minutes, and the phase, or relative position, in these periods, during which the obtained measurement(s) are instantaneously found.

The implementation of this program effectuates a filtration of the obtained value from each sensor and provides a relative position of the said value in the cycle representing a temporal variation of a non-sensory biological activity, the said cycle being of duration greater than one minute.

The means of display includes at least one display zone of the immediate relative position in a cycle detected by the means of frequency analysis. In the embodiment depicted in FIG. 5, the immediate relative position is represented, on one hand, by a percentage of the cycle gone by, using the four characters in the means of display 502, and, on the other hand, by the position of the supplementary watch hand in the means of display 502, that percentage and that position being for example the lowest (0% and watch hand positioned at six o'clock) when the phase corresponds to an angle of less than 90 degrees (the bottoms of the curves illustrated in FIG. 11C).

Figure 6:
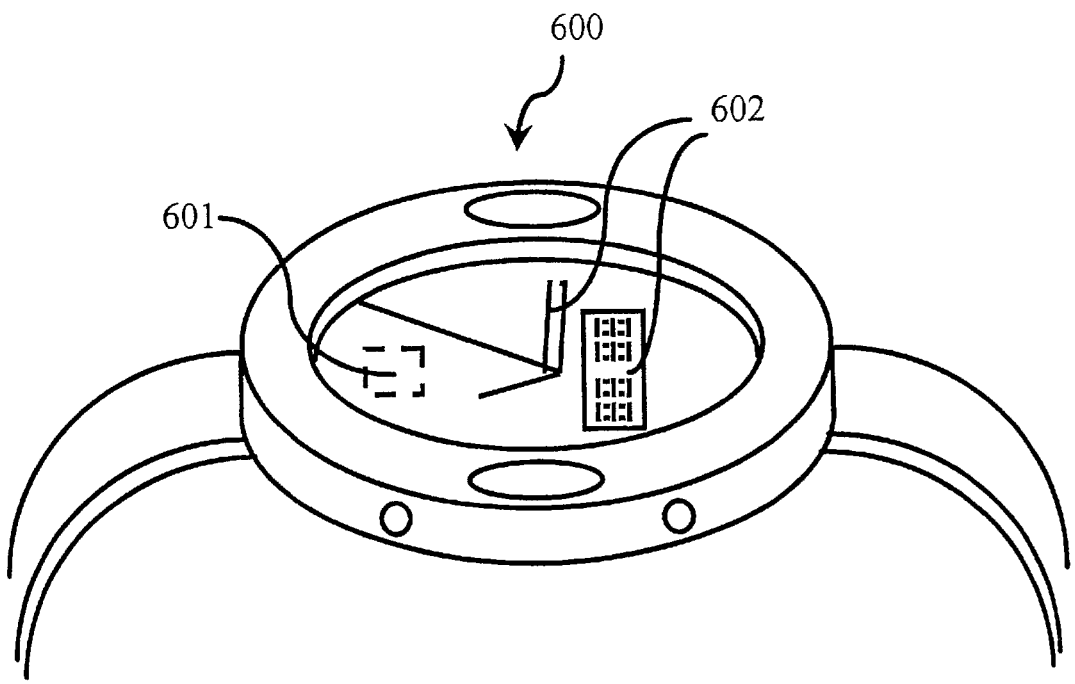
FIG. 6 represents a view from above, in perspective, of a fourth embodiment of the device described by the present invention, incorporated in a watch.

FIG. 6 depicts a view from above, in perspective, of a fourth embodiment of the device of the present invention, incorporated in a watch. This embodiment of the present invention includes all the elements of a tension meter 600 designed to be permanently worn on a wrist, and to which has been added a memory 601 that stores a program for the functioning of the device and a means of displaying the relative position in the biological cycle 602, of the same sort as the means of display 502.

Two programs are added to the memory, besides the ones that allow for the functioning of the traditional watch. The first program controls the measuring of movement (represented by the number of wrist movements), at regular time intervals, for example four times per minute, each value obtained being a total number of movements made during this time interval. This program writes the results of these measurements to memory.

The second program is a program that performs a frequency analysis on the variations in the pulse and/or the arterial pressure (in particular, the systolic pressure) designed to detect periods of variation in movement greater than one minute and less than twelve hours. Preferably, this program detects periods between ten and two hundred minutes, and the phase, in these periods, during which the obtained measurement(s) are instantaneously found.

The implementation of this program effectuates a filtration of the obtained value from each sensor and provides a relative position of the said value in the cycle representing a temporal variation of a non-sensory biological activity, the said cycle being of duration greater than one minute.

The means of display includes at least one display zone of the immediate relative position, or phase, in a cycle detected by the means of frequency analysis.

It should be observed here that a means to embody an actimeter is given by modifying an "automatic" watch, that is by adding a spring that compresses according to the movement of the wrist, the said spring being mounted on an shaft connected to a piezoelectric crystal in such a manner that the spring tension is represented by the tension (voltage) at the terminals of the piezoelectric crystals, and by configuring the watch hands in such a manner that the spring is extended during a duration less than the considered cycle.

The signal as it exits the piezoelectric crystals is therefore the one that is used to measure the average activity over the period of time that the spring is extended.

According to one variation, the watch hand in the means of display 602 is connected to the output of the spring and the position of the hand turns according to trigonometric methods for each movement that has sufficient intensity to compress the spring, and according to the method of a traditional watch hand between two movements. The angles of rotation in each method are pre-calculated so that in a given cycle, for example one day, going from the position of four o'clock, at the wake up time, the watch hand moves throughout the course of the day towards the position eight o'clock, by passing the position at noon and does not return to the position at four o'clock until the following night. According to this variation, the position of the hand represents the potential of normal activity still available to the user. This potential increases (clockwise) each time the user rests.

In this variation, a means to adjust the rotation of the watch hand that corresponds to each movement is designed to be adapted to the user's activity level. According to one variation, this angle varies and becomes smaller and smaller as the hand approaches the eight o'clock position which corresponds to a minimal activity potential. This latter characteristic can be realized by using a counter spring that pulls the hand in the means of display 602 towards the four o'clock position, and, at the same time, as the spring gets compressed by the arm movements, it pulls this same band towards the eight o'clock position, and gets progressively extended as time passes, by being linked to its other extremity, for example, to one of the hands that indicate the time.

In this embodiment:

an information intake system that obtains values representing a non-sensory biologcal activity of the user's body includes a mechanism to compress the spring, similar to those in an "automatic" watch, a means of filtration of the value obtained by the said information intake system includes a counter spring and spontaneous extension of the spring as in an automatic watch; this means of filtration provides a relative position of the said value in the cycle representing a temporal variation in the said non-sensory biological activity, the said cycle possessing a duration of one day, and a means to allow the user to know the information representing the said relative position including a watch hand that moves between two extreme positions.

According to another embodiment (not depicted), three inertia blocks are each positioned at the extremity of a piezoelectric linear crystal, where these three piezoelectric linear crystals are oriented along three perpendicular axes. The electric tensions coming from these crystals are sent to an analog numeric converter or to a binary signal input, in such a manner that a wrist movement that would occur in typing on a keyboard, for example, would be detected as a nonzero tension.

In each of these four embodiments, as illustrated in FIGS. 1 to 6, the user can program:

either a maximum wake up time, before which he or she would like to be awakened, either a number of sleep cycles which he or she wishes to experience, either a simple visualization of the instantaneous phase in the cycle in progress, without wanting to be awakened.

To this effect, the user pushes the buttons 107 and follows the instructions on the display (for example 106, 502, or 602).

Figure 7:
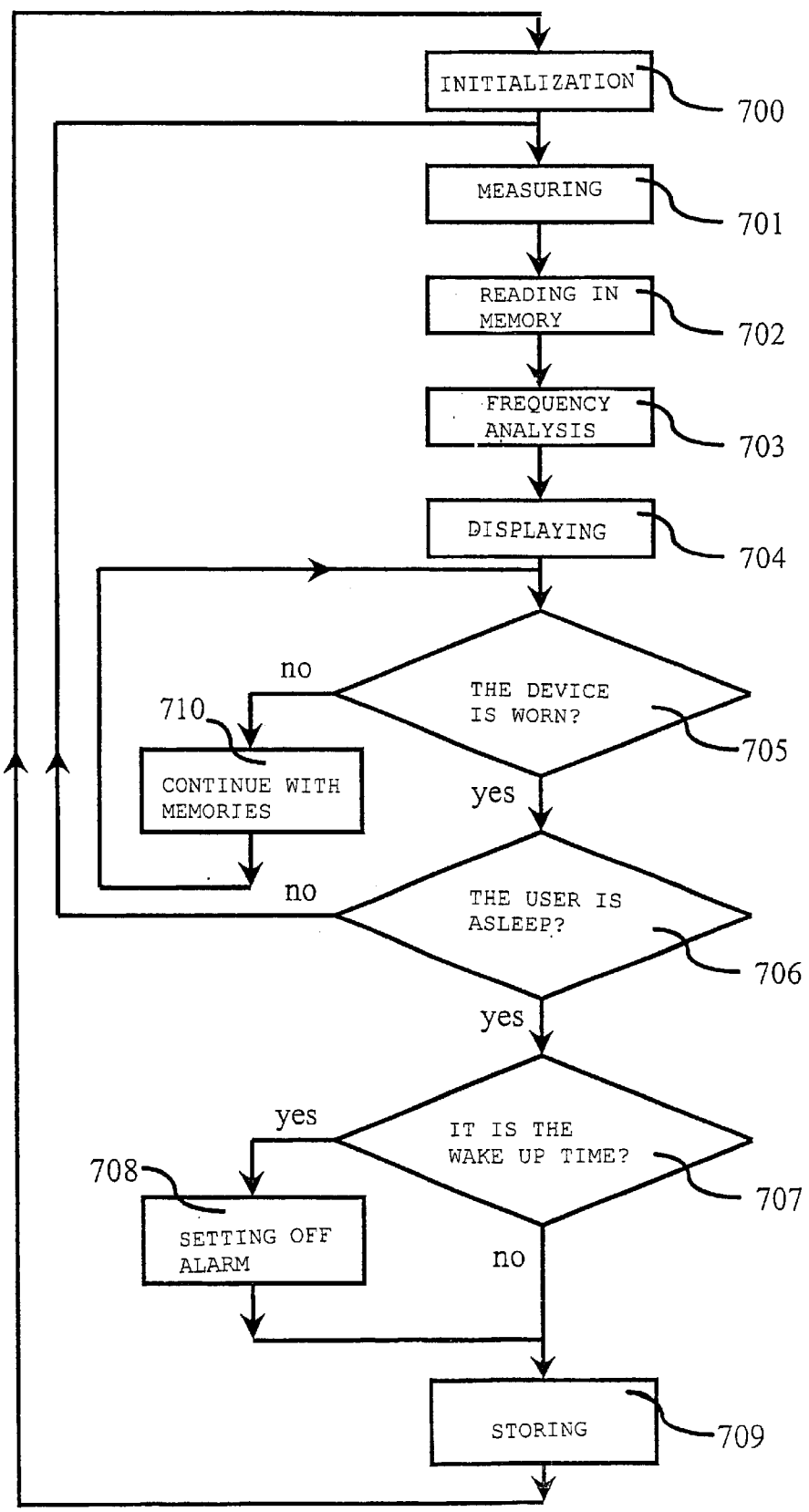
FIG. 7 represents a flow chart of the third and fourth embodiments of the present invention, as they are illustrated in FIGS. 5 and 6.

FIG. 7 depicts a flow chart for the third and fourth embodiments.

After an initialization operation 700, begun, for example, by the user pushing a certain button on the device, or by the detection of certain values of the natural state (for example, pulse, tension, or motion) that do not correspond to a period of sleep (see test 706 herein), the central processing unit of the device effectuates a measurement 701 of the natural state.

Then, during operation 702, the central processing unit effectuates a reading into memory of:

the average value of the natural state at the same time as the preceding day, the principle period detected during the preceding day, according to the moment of the day (wakefulness, from 10 o'clock in the morning to 10 o'clock at night, and sleep, detected by the small variations of values of the considered natural state), and the rate of reliability observed during this period, that is the average amplitude of the crests of the frequency analysis (see operation 703).

Next, during operation 703, the central processing unit effectuates a frequency analysis of the results of the measurements obtained in operation 701, taking into account the average value on one hand, and the read period, on the other hand.

This frequency analysis provides three givens:

a rate of reliability of the other results of the analysis (the rate depends on the number of measurements taken since the initialization 700, and on the average crest value observed since the initialization 700), a principle period (duration of a cycle) measured since the initialization, and the instantaneous phase in the cycle of variation of the considered natural state that presents the said period.

During operation 704, the central processing unit instructs the means of display to display information representative of the instantaneous phase, for example by positioning the hand (502 or 602, in the embodiments depicted in FIGS. 5 and 6) designed for such use, on the watch dial.

During test 705, the central processing unit determines whether or not the device is worn by the user, by determining whether or not measurements of the natural state are possible (values of zero for pulse or for arterial pressure or values of zero for activity during a period of more than 30 minutes indicate, for example, that the user has ceased to wear the device).

If the result of test 705 is negative (the device is not being worn), the central processing unit determines at what time, on average, the user has fallen asleep throughout the course of the last week and the displaying of the phase is pursued in operation 710. For the display, the central processing unit keeps track of the instantaneous time in regards to the average falling asleep time, the previous value of the period of the considered cycle, before the average falling asleep time, and after the average falling asleep time, and of the average value of the duration of the sleep cycle stored in memory, by considering that the phase evolves regularly in day and night cycles. Therefore, before the average falling asleep time, the displayed phase is the result of the continuation of the regular evolution of the day phase, while after this average hour, the phase returns to its maximum value, then evolves regularly with a cyclical period equal to the nocturnal evolution period stored in memory. After each driving operation of the means of display (502 or 602, for example), that last for a fraction of a second, the operation 705 is repeated.

If the result of test 705 is positive, then during the test 706, the central processing unit determines whether or not the user is asleep, based on the last values of the considered natural state. If the result of test 706 is negative, operation 701 is repeated. If the result of test 706 is positive, then during test 707, the central processing unit determines whether or not it is the programmed wake up time, the said programmed wake up time being:

- a time chosen by the user from among different times corresponding to sleep cycles and proposed by the device,
- corrected to correspond to the effective end of a sleep cycle.

If the result of test 707 is positive, an alarm is set off for thirty seconds, during operation 708. At the end of operation 708 or if the result of test 707 is negative, then during operation 709:

- the falling asleep time is placed in memory,
- the average value of the day cycle is placed in memory, and the contents of test 706 are modified in such a manner that the output of this test are reversed, and
- operation 700 is repeated.

If the result of the next test 706 is positive, if the user has awakened, at a time corresponding to a normal duration of sleep for the particular user:

- the wake up time is placed in memory,
- the average value of the nocturnal cycle is placed in memory, and the contents of test 706 are modified in such a manner that the output of this test are reversed, and
- operation 700 is repeated, and so forth.

Figure 8:
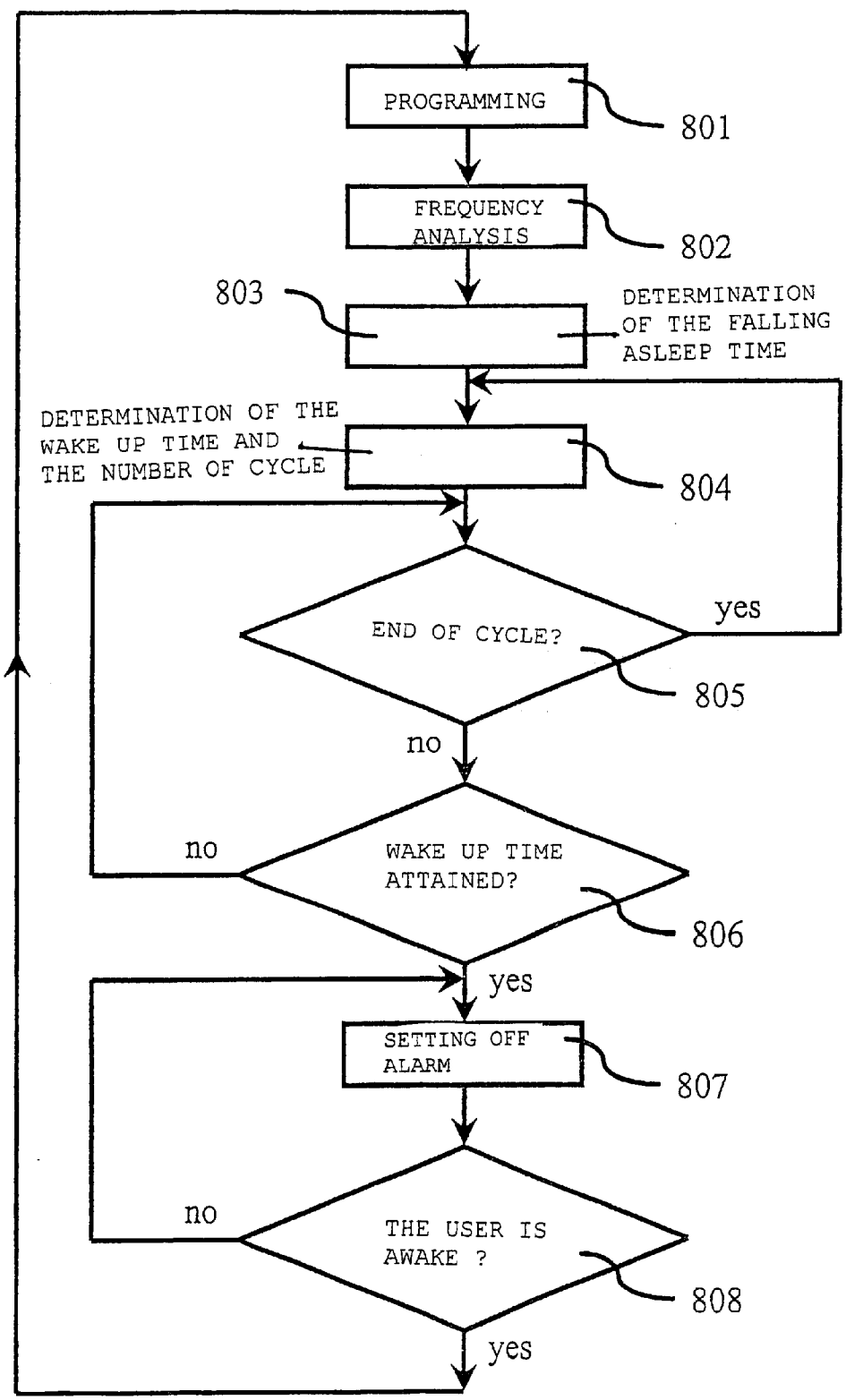
FIG. 8 represents a flow chart of the four embodiments of the present invention, as they are illustrated in FIGS. 1 through 6.

FIG. 8 depicts a flow chart of the functioning of the four embodiments of the present invention, as they are depicted in FIGS. 1 to 6.

In FIG. 8, it can be observed that, after the selection of a number of sleep cycles or of a maximum wake up time, operation 801, the central processing unit proceeds to a frequency analysis (see FIGS. 11A to 11C), operation 802.

Next, the central processing unit proceeds to the determination of the falling asleep time (see FIG. 11D), operation 803. When the fall asleep time is detected, and when the period of the sleep cycle is determined, the central processing unit proceeds, during operation 804, to the determination of the wake up time and the number of sleep cycles the user wants:

- by adding the product of the number of cycles programmed by the user and the cyclic period, at the fall asleep time, when the functioning mode is the programming of a number of cycles, or
- by determining the previous end of a cycle that preceded the maximum wake up time programmed by the user.

At the end of each cycle detected during test 805, operation 804 is repeated to improve the estimation of the wake up time.

When the wake up time is attained, a sound or vibratory alarm attempts to awaken the user, until the user pushes one of the buttons 107, operation 806.

Next, during test 807, the central processing unit determines whether or not the change in the observed natural state, for example the pulse or muscular activity, correspond to a state of wakefulness (the pulse must, on average, increase by more than ten percent and the number of arm movements detected by more than 100 percent). If, during test 807, the central processing unit determines that the user is not awake, operation 806 is repeated immediately, without waiting for the end of a sleep cycle.

According to a non-depicted variation, operation 806 is repeated to awaken the user at the end of the next sleep cycle.

Next, operation 801 is repeated.

Figure 9:
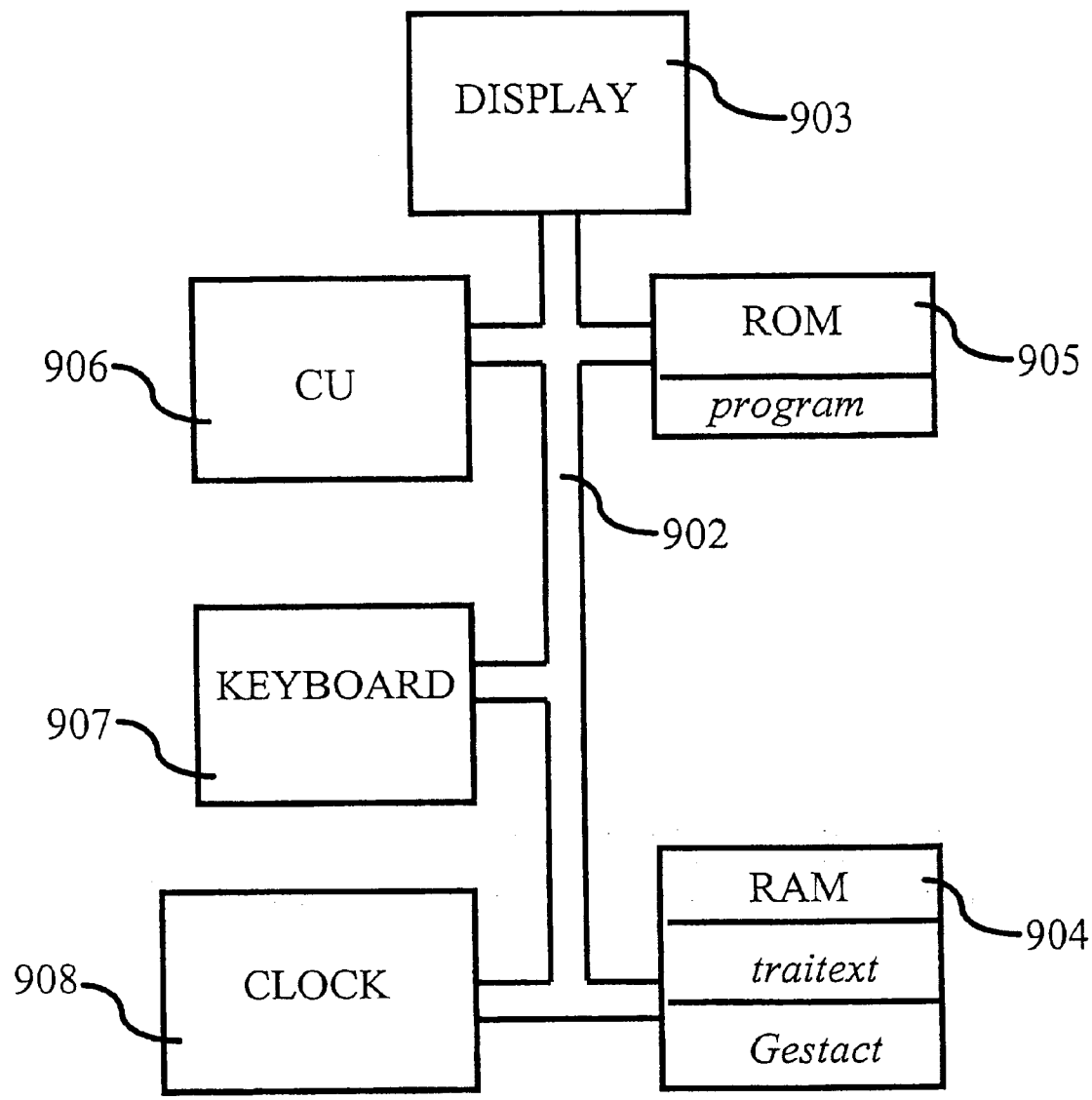
FIG. 9 represents a fifth embodiment of the present invention.

FIG. 9 depicts a fifth embodiment of the present invention, which is nothing more than a computer, where the keyboard serves as a sensor of the user's arm activity, the said computer storing, in memory, a specific program of frequency analysis of the speed of the keystrokes of the user and the determination of cycles of keystrokes on the keyboard.

Around the bus 902 and a clock 908, a central processing unit 906 manages a keyboard 907, a read only memory 905, a random access memory 904, and a monitor 903.

The random access memory 904 stores a program to process text "traitext" 901 and a program to manage periods of activity "gestact" 909, that functions as a background task, with regard to the processing of text.

The central processing unit 904 functions on a multitask level. The processing of text is of a known type.

The program to manage periods of activity "gestact" 909 functions with the principle that, when a user types on a keyboard, the average rhythm of a stroke (in terms of average duration between two successive strokes, not counting periods of reflection, or in terms of number of strokes per minute, including periods of reflection) is representative of the phase of the biological cycle the user is currently experiencing. Also, the number of mistakes, or corrected keystrokes, or backspaces are representative of this phase, which can be used in a variation of an implementation of the present invention.

Figure 10:
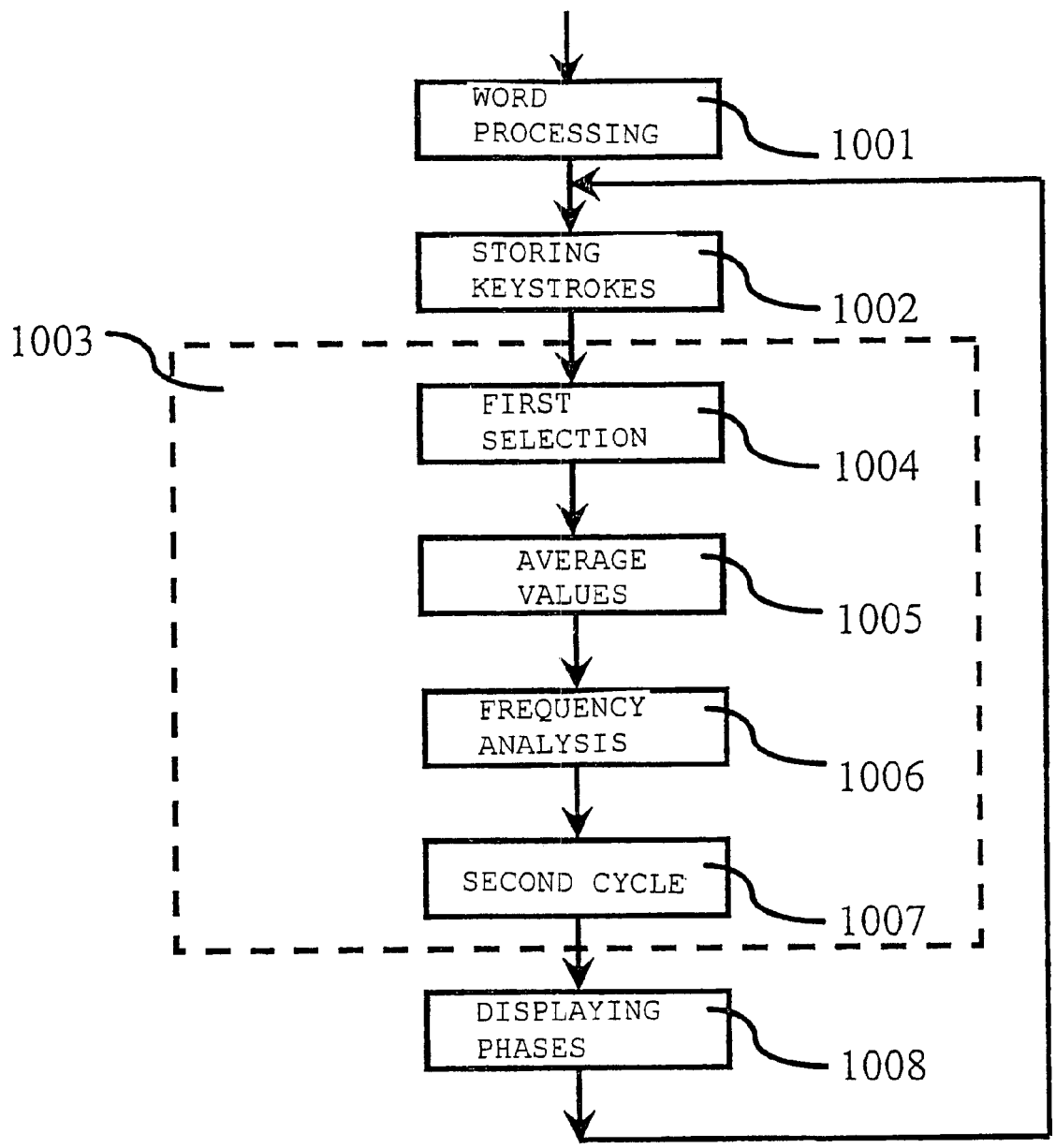
FIG. 10 represents a flow chart of the fifth embodiment of the present invention.

The program to manage periods of activity "gestact" functions as follows (FIG. 10):

- after having put to use the program to process text, operation 1001,
- as a background task, the central processing unit 906 memorizes, on one hand, the value of the clock, at each keystroke on the keyboard, and, on the other hand, the number of keystrokes used to correct faulty keystrokes (by only counting "backspace" and "delete"), operation 1002,
- next, the memorized values are analyzed, during operation 1003, as follows:
- the durations between two keystrokes is determined, and all durations greater than twice the average of these durations are eliminated, and the operation is repeated until the sample of durations are stabilized (this constitutes a first selection), operation 1004;
- at the end of each minute, an average value from the durations resulting from the first selection is assigned, and a "weight" corresponding to the number of durations left in the considered minute is assigned, operation 1005;
- these givens are analyzed as indicated in FIGS. 11A to 11D, operation 1006.

This provides a cycle linked to the speed of the keystroke, knowing that the user is preliminarily told that he or she should try to optimize the speed of his or her typing.

A second cycle is provided by the analyzing of the number of keystrokes made per minute, in the same manner as is depicted in FIGS. 11A to 11D, operation 1007.

According to one variation, which has value only in the case where the processing of text creates a new file without opening other files, only the corrections of mistakes are counted and they are analyzed in the same manner as the durations between keystrokes as described herein.

The phases in the cycle are displayed in two circular dials, one linked to the number of keystrokes made, a cycle called "intellectual," and the other linked to the speed of the keystrokes, a cycle called "physical."

Figure 11A:
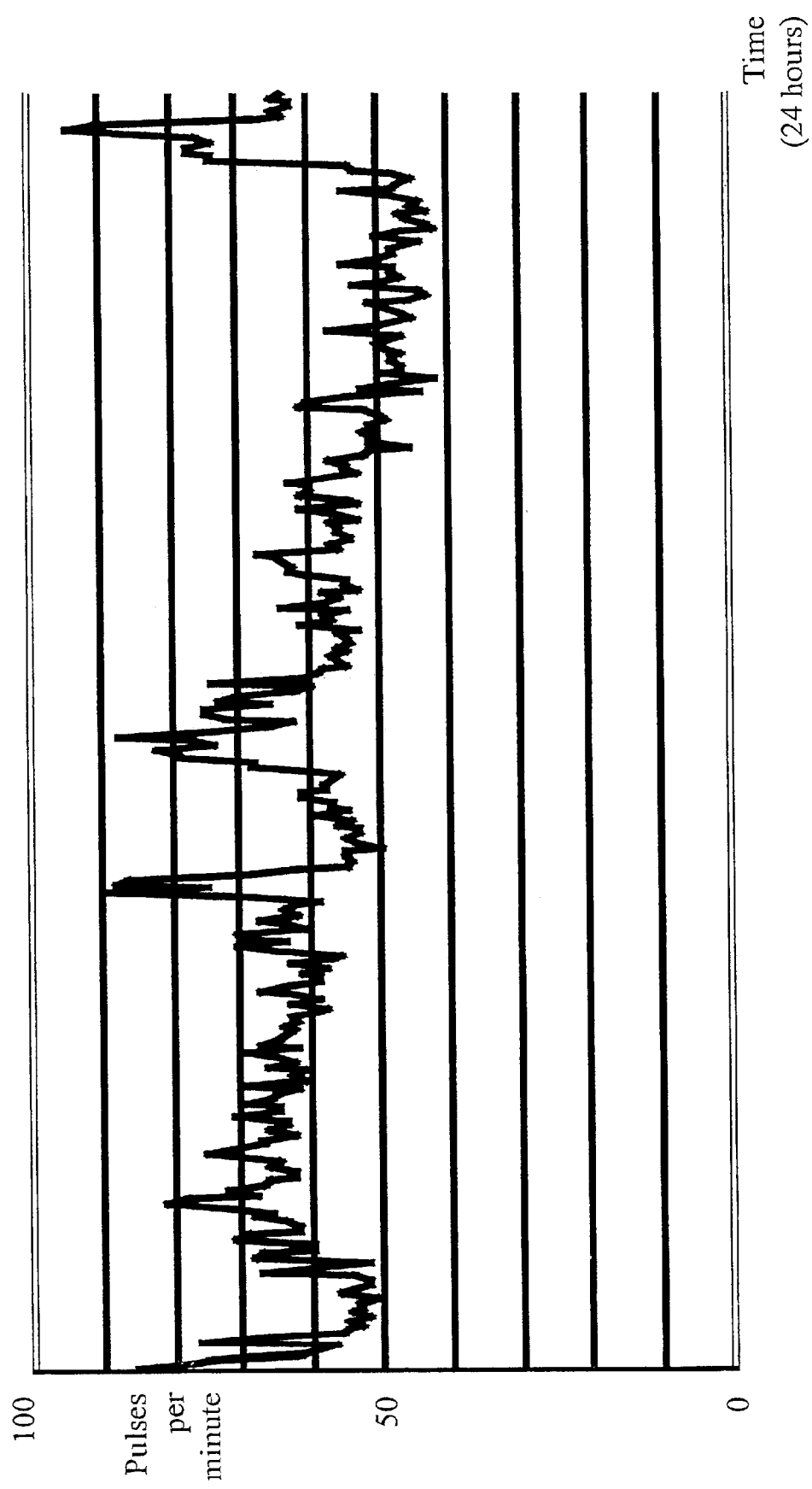
FIGS. 11A, 11B, 11C and 11D represent cardiac frequency curves being processed in accordance with an embodiment of the present invention.
Figure 11B:
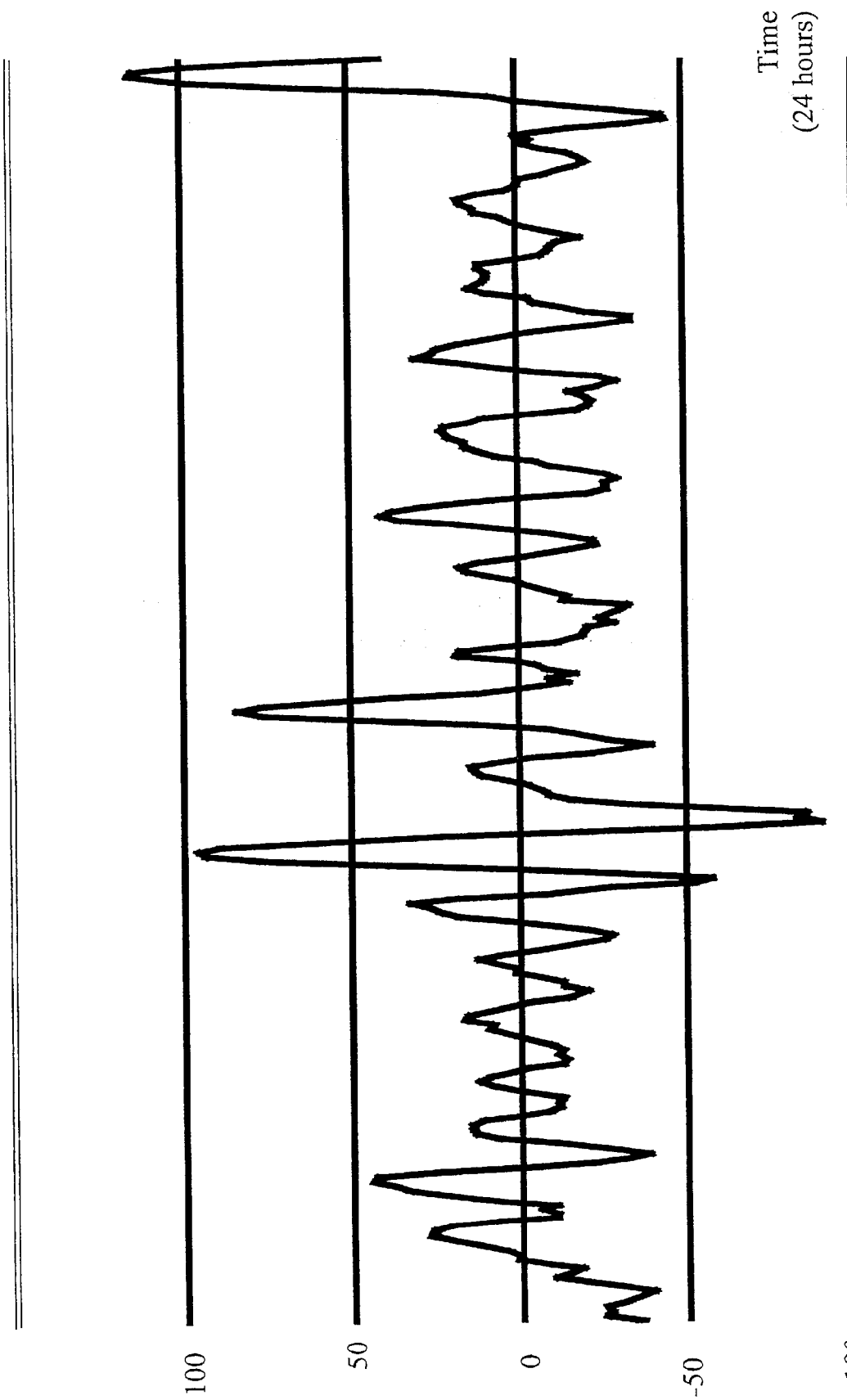
Figure 11C:
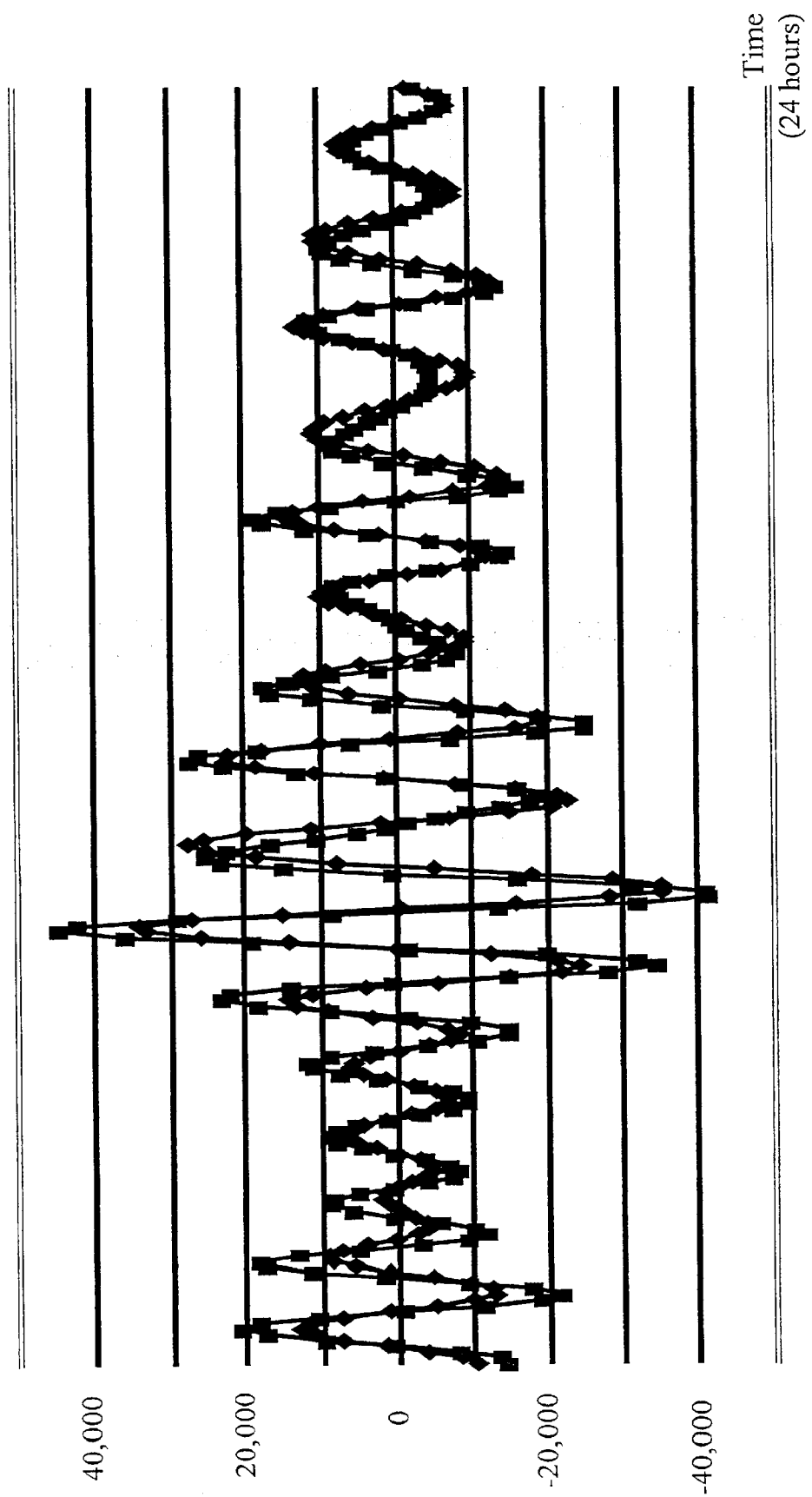

FIGS. 11A, 11B, and 11C represent cardiac frequency curves being processed according to an embodiment of the present invention.

In FIG. 11A, the curve depicted is known by cardiologists by the name "Holter," which is the name of the inventor of the portable apparatus that permits the capturing of cardiac activity during an entire day.

The successive samples, along the x-axis, each correspond to a duration of five minutes and to three values representing the maximum value of the cardiac frequency during the sample of five minutes, the average value of the cardiac frequency during the sample of five minutes, the minimum value of the cardiac frequency during the sample of five minutes.

The x-axis represents the hours (between twelve hours of one day and twelve hours the next day) and the y-axis represents the cardiac frequencies. The user in this case is around thirty years old.

In the following, only the average values of the cardiac frequencies are used, even though each of the other series of values could provide the same results.

FIG. 11B represents the results of a filtration by a sinusoid with a frequency of 80 minutes (16 samples over one sinusoid) over the series represented by the average values. The result is a reduced series (eight samples are lost at each end) that shows oscillations that are fairly regular, day and night.

In FIG. 11C, the same filtration was used four times, recurrently, and produced the curve where the points are represented by slanted squares. In the same figure, a sinusoidal filter with a frequency of 70 minutes (14 samples per sinusoid) was used in a recurrent manner four times over the series of average values of the cardiac frequencies and produced the curve possessing the upright squares.

It can be seen that the two curves produced cycles in which the successive amplitudes are not identical but in which the periods and phases are reasonably equal and could be determined by a simple trigonometric analysis.

Figure 11D:
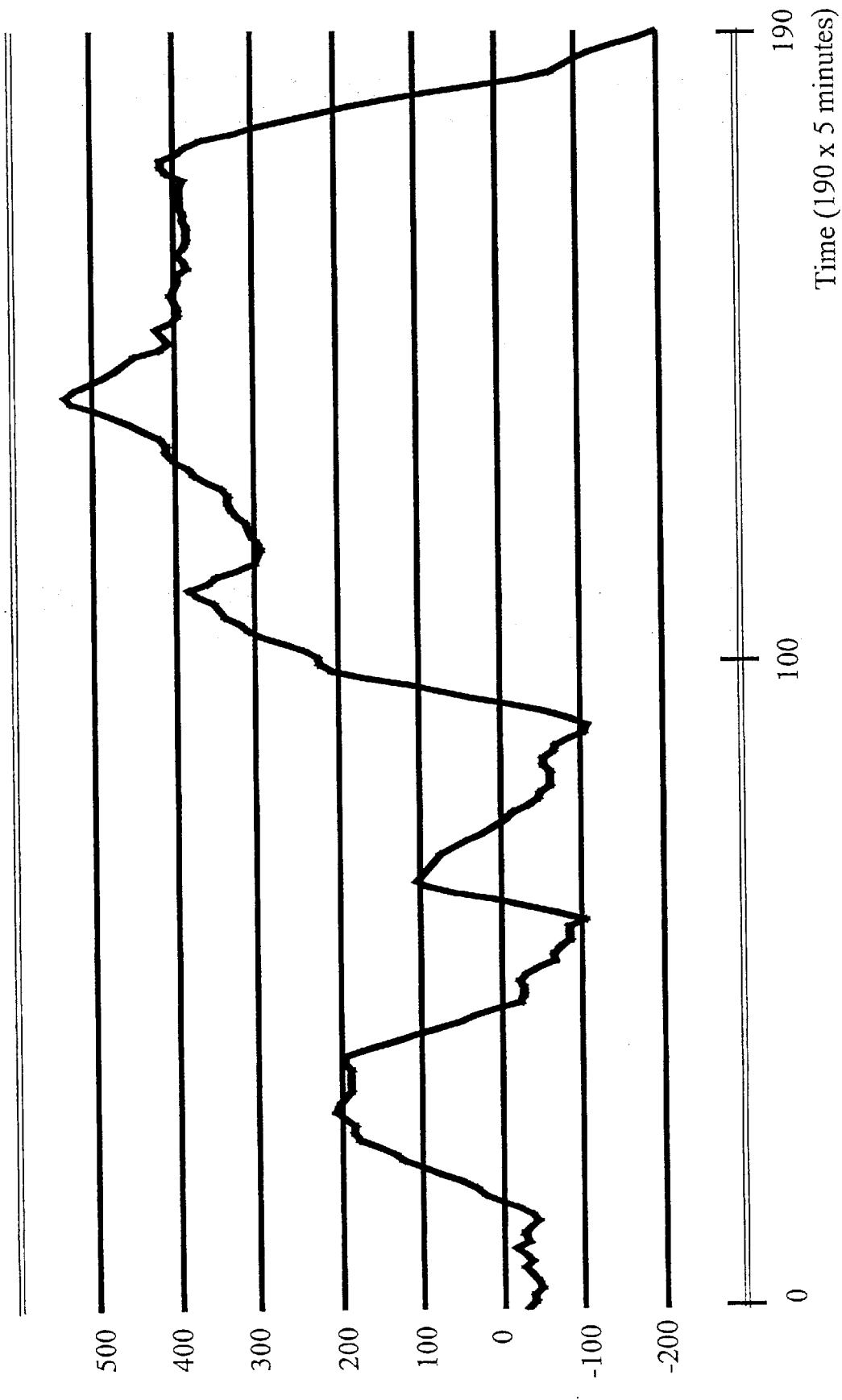

In FIG. 11D, it should be observed that the difference between the forty-eight values that precede a sample and the forty-eight values that succeed it show a characteristic form at the moment of falling asleep: the curve becomes positive during a duration of more than seven successive hours.

Here, the falling asleep time corresponds to the passing above the greatest value of the difference, observed during the day (around 200). It happens at the sample of approximately 97, knowing that forty-eight samples were lost at each end of the series.

In one variation, to determine the amount of activity, it is the average intensities of electric currents in the arm that wears the device (if the device is in the form of a watch) that provides the analyzed natural state.

According to another variation, the information intake system is placed in a shirt pocket and detects the heartbeat, by sound or by electric current, or also in the same manner as sensors designed for runners, of the brand "POLAR" (registered trademark) or "CARDIOSPORT" (registered trademark generally associated with the registered trademark "C.A.R.E." which relates to home exercise equipment).

In a non-depicted embodiment, the processor determines an integral of the difference between the value obtained by the information intake system, for example the number of movements detected by an actimeter, and the average value for the same phase as a preceding cycle, for example, the cycle corresponding to the preceding day. The means of display therefore displays the value of this integral, for comparison purposes. The value of this integral is representative of the relative position in the cycle of variation of the obtained value since, in the absence of activity, this integral varies as a function of the position in the cycle.

This embodiment, which can be integrated into the fourth embodiment (FIG. 6), is particularly useful during the training of a user for an activity represented by the obtained value, for example when this training concerns the keystrokes on an alphanumeric keyboard, a physical exercise such as running, a cardiac activity, or the mastery of cerebral electric wave emissions.

This embodiment also allows a still available potential for activity to be put to the user's disposal, in addition to or in subtraction of the average activity during a cycle.

In a non-depicted embodiment, to determine a cycle and a position in a cycle of a duration going from 60 to 100 minutes, three frequency filtrations are effectuated by convolution (correlation) with three sinusoids of durations equal to, respectively, 60, 80, and 100 minutes, and the sum of the resulting curves is taken.

It should be observed that, in this embodiment, when the three phases after correlation are the most identical, the relative position that corresponds to this phase is the best adjusted and it is used as a reference. The other relative positions are then adjusted according to this reference position.

In a non-depicted embodiment, the end of a profound sleep cycle is detected, without determining the duration of the sleep cycle, and the number of cycle endings already detected within the same night are counted, and the user is awakened when the number attains a value determined by the user, or when the projection, by linear regression, of the next cycle ending will occur later than the maximum wake up time that the user has chosen.

The present invention can also take on numerous forms adapted to familiar objects. For example, one embodiment could take the form of a ring incorporating a sensor of blood pressure, pulse, muscular activity, or temperature, and would display the relative position in a cycle of variation of the obtained value by simply changing color.

In another embodiment, not depicted, an earring can sense the pulse on the ear lobe, in a known manner, and can cause an audible vibration for certain relative positions in the cycle of variation of the pulse, or to awaken the user.

In another embodiment, not depicted, glasses can sense the pulse, using as intermediary the blood vessels on which the glasses frame rests, or sense electric cerebral waves.

In another embodiment, not depicted, headphones can sense the pulse, using as intermediary the blood vessels in the ear, in which the blood flow causes, on one hand, an audible sound, and, on the other hand, a rise in temperature, or sense electric cerebral waves.

In another embodiment, not depicted, a motion sensor of known type in the field of alarms and surveillance equipment, detects the movements of the sleeper, or of the static worker, his or her movements being representative of at least one biological clock.

In one variation, when the user changes the time on his watch by more than sixty minutes, that is if he or she has crossed more than one time zone, the curves are slowly shifted to the new time, by shifting them by one hour each day to take into account the progressive adaptation of the human body to a shifted schedule.

According to a non-depicted variation, the device envisioned by the present invention includes an interface with a light generation system, such as a lamp or a window shade, and when the wake up time is attained, the light shining on the eyes of the user is intensified either progressively or suddenly.

For example, for the implementation of the present invention in airplanes, light-emitting diodes placed in glasses facing the user's eyes sense, at a distance, the movements of the user's eyes, for example, by analyzing the dispersion of invisible luminescent waves reflected off the eyelids.

In one variation, not depicted, the information intake system is adapted to sense the sound vibrations of the heartbeats, by being placed inside the shirt pocket in front of the user's heart.

According to a non-depicted variation, the means of display displays the next time at which a sleep cycle could favorably begin and the favorable wake up times that will result (for example the favorable wake up times after at least five sleep cycles).

It should be observed that a statistical analysis can replace the frequency analysis described herein in order to be clear.

According to a non-depicted variation, the information intake system is designed to determine a conductivity value of the skin surface. For the implementation of this variation, the reader can refer to document WO 93 16636 that is included herein for reference.

According to a variation of each of the embodiments represented in the figures, the information intake system is designed to provide a value when it is in a predetermined relation with the user's body, the means of filtration includes:
 a memory for values obtained by the said information intake system,
 a means of estimation of the said position when the information intake system is not in the predetermined relation with the user's body; this means being, for example, the search for a regular cycle, by storing the previous value of the determined cycle duration or a duration following a variation of durations that are observed over the preceding determined durations, and the means of implementation is designed to allow the user to know the said estimation.

It should be observed that in the different embodiments that do not implement the circadian cycle, the information intake system that obtains values representing a non-sensory biological activity of the user's body is designed to obtain a number of biological events (for example movements, heartbeats, respiratory movement), and the means of filtration is designed to determine the duration of a cycle at least ten times greater than the average duration between two events sensed by the sensor.

In a variation of each embodiment using a microprocessor, the device includes a memory that stores a cycle duration and the microprocessor is designed to determine a cycle duration by processing the obtained value, and to compare the determined cycle duration to the cycle duration stored in the memory. When the determined cycle duration is greater than the cycle duration stored in the memory, the processor determines the relative position to display in comparison to the previous determined cycle duration determined by the means of filtration or, in a variation, to the cycle duration stored in the memory.

To implement the variations of the different embodiments illustrated herein, the reader can refer to:

document EP 0 778 003 which relates to a presence detecting apparatus that allows, in particular, the detection of movements of a person, in a bed where two people are found. This document is incorporated herein for reference;

document U.S. Pat. No. 4,299,233 which presents a patient surveillance device and that shows means of motion detection involving a bed. This document is incorporated herein for reference;

document U.S. Pat. No. 5,446,775 which presents a movement detector/counter involving a watch. This document is incorporated herein for reference;

document EP 0 729 726 which presents a pulse measuring device involving a watch and a ring. This document is incorporated herein for reference;

In another embodiment of the present invention, a display dial is used similar to that of the first embodiment of the present invention, involving a watch.

In this embodiment, which includes the same components of the first embodiment, the biological clock that is implemented is circadian. The information intake system that obtains a value representing a non-sensory biological activity of the user's body is in this case a temperature sensor that is placed in contact with the user's skin and that detects the rising of the temperature of the watch's surface that is in contact with the user's skin, following the placement of the watch on the wrist, after several hours of sleep during which the watch was at the ambient temperature. The biological activity is in this case the physical activity following the arising of the user.

The watch incorporating the device envisioned by the present invention is designed, when the user implements the buttons (see buttons 107 of the first embodiment), to display successively:

time since awakening;
 speed of research;
 speed of reasoning;
 vigilance;
 dexterity;
 overall vigor;
 overall feeling (of well-being);
 concentration of melatonin (the sensation of needing to sleep);
 internal temperature.

The instantaneous levels of each of these parameters is stored in the read only memory and each relative position following awakening is compared with the instantaneous value of each parameter for the displaying of this instantaneous level.

One skilled in the art can refer to the works of the sleep center and the chronobiology of the psychiatric department of the School of Medicine at the University of Pittsburg, 3811 O'Hara Street. In particular, the article "Endogenous Circadian Performance Rhythms—Relationship to Temperature, Cortisol, Melatonin, Mood, and Alertness" of the book "Biological Clocks" cited above shows exploitable curves and interpretations of these curves.

In a preferred embodiment, the means of display displays several values simultaneously. For example, several watch hands, partially transparent, each represent an instantaneous level in the curve of one of the considered parameters.

In a variation of this embodiment, a variation that corresponds to another aspect of the present invention, no information intake system is implemented and the device implements the considered curves, in direct relation with the time, independently of the wake up time.

It should be observed here that all or part of these values are independent of the wake up time of the user and depend only on the instantaneous time and/or depend only slightly on the wake up time. Some simple experiments will allow a table of correspondence to be determined, for each value to be displayed with the instantaneous time and the wake up time.

The device therefore allows the parameters variable over a regular cycle to be displayed, and includes:

a memory of values of each of these parameters;

a clock that provides the time, a means to compare the time provided by the clock with at least one value of a parameter, and a means of display of at least one value compared with the time provided by the clock.

In a variation of this previous variation, the user can select his or her wake up time to take into account his habits. The comparison with the curves of the parameters cited above will be therefore shifted from the shifting of the habitual wake up time in comparison to the average person. For example, a user that regularly awakens at 9 o'clock in the morning will have his curves shifted later by two hours in comparison to a user habituated to awakening at 7 o'clock in the morning.

What is claimed is:

1. A method to allow a user to know information, that includes:

a step of obtaining instant values each representing an instant non-sensory biological activity of the user's body, a step of filtration of the obtained instant values to determine a duration of a cycle representing a temporal variation of said non-sensory biological activity, based on at least two obtained instant values, the duration of the cycle being more than one minute and less than a circadian cycle, and to provide an instant relative position of said value in the cycle, and a step of instantly providing the user with an instant information representing said instant relative position.

2. A device that allows a user to know information relating to the user's biological activity, the device including:

an information intake system that provides instant values each representing an instant non-sensory biological activity of the user's body, a filter that filters said instant values obtained by said information intake system, and determines a duration of a cycle representing a temporal variation of said non-sensory biological activity, based on at least two instant values, the duration of the cycle being more than one minute and less than a circadian cycle, the filter that provides an instant relative position of said value in the cycle, and an output system that instantly provides the user with an instant information representing said instant relative position.

3. The device of claim 2, wherein the information intake system provides instant values that each represents instant muscular activity of at least one limb of the user.

4. The device of claim 3, wherein the information intake system provides instant values that each represents a rubbing of the user's body on a surface.

5. The device of claim 2, wherein the filter integrates a difference of the obtained instant values with a predetermined value and provides the instant relative position in the form of a relative position of said integral in an array of values of said integral.

6. The device of claim 2, wherein the information intake system obtains instant values each representing a non-sensory biological activity of the user's body, without bilateral contact with the human body.

7. The device of claim 2, wherein the information intake system obtains instant values each representing a cardiovascular activity of the user's body.

8. The device of claim 2, wherein:

the information intake system provides instant values when the information intake system is in a predetermined relation with the user's body, the filter includes:

a memory of values obtained by said information intake system, an estimator that provides an estimation of said instant relative position when the information intake system is not in the predetermined relation with the user's body, and the output system provides the user with said estimation when the information intake system is not in the predetermined relation with the user's body.

9. The device of claim 2, that includes a memory of a predetermined position in said cycle, wherein the output system provides a signal when said instant relative position is equal to said predetermined position.

10. The device of claim 2, wherein the filter includes a processor that effectuates a frequency analysis of obtained instant values.

11. The device of claim 2, wherein the information intake system provides a number of biological events, and the filter determines the duration of a cycle of at least ten times greater than the average duration between two events obtained by the information intake system.

12. The device of claim 2, wherein the information intake system provides durations separating keystrokes on a keyboard.

13. The device of claim 2, wherein the information intake system provides the instant values each representing a non-sensory biological activity of the user's body when the information intake system is positioned at a remote position from the user's body, the instant values each representing movements of the user's body.

14. The device of claim 2, wherein the output system includes a memory of stored values respectively corresponding to relative positions in the cycle, and displays, for each relative position, the stored value corresponding to the instant relative position provided by the filter.

15. The device of claim 2, that includes a memory of a duration of a cycle, wherein the filter determines the duration of the cycle, compares the determined duration of the cycle to the duration stored in the memory of the duration of a cycle, and, when the determined duration of the cycle is greater than this duration stored in the memory of the duration of a cycle, determines the relative position in comparison to the duration stored in the memory of a duration of a cycle or to a previous cycle duration determined by the filter.

16. The device of claim 2, that includes a memory that stores a predetermined relative position, the output system that displays a time at which said predetermined relative position will be attained.

17. The device of claim 2, wherein the filter detects the coming of a reference position in the cycle, and provides the relative position in relation with the reference position.

18. The device of claim 2, wherein the filter:

tests a first value of a cycle duration, called period, by detecting the cycles of variation of said instant values, and if the number of detected cycles, during a reference duration given by taking into account said period, is greater than the ratio of the reference duration over said period, tests a new shorter cycle duration, if the number of detected cycles, during a reference duration given by taking into account said period, is less than the ratio of the reference duration over said period, tests a new longer cycle duration, and so forth until the number of detected cycles is equal to said ratio.

19. The device of claim 2, wherein the information intake system is incorporated in an object selected from the group consisting of jewelry, a pillow, a bed, a motion or presence detector, a piece of clothing, glasses and headphones.

* * * * *